United States Patent
Horiuchi et al.

(10) Patent No.: US 12,284,958 B2
(45) Date of Patent: Apr. 29, 2025

(54) **CYTOPLASMIC MALE STERILE *BRASSICA RAPA* PLANT HAVING IMPROVED GROWTH ABILITY**

(71) Applicant: SAKATA SEED CORPORATION, Yokohama (JP)

(72) Inventors: Shingo Horiuchi, Kanagawa (JP); Takao Suzuki, Kanagawa (JP); Atsushi Izumida, Kanagawa (JP); Kazuhiro Nishikawa, Kanagawa (JP)

(73) Assignee: SAKATA SEED CORPORATION (JP)

( * ) Notice: Subject to any disclaimer, the term of this patent is extended or adjusted under 35 U.S.C. 154(b) by 323 days.

(21) Appl. No.: 17/604,200

(22) PCT Filed: Apr. 17, 2020

(86) PCT No.: PCT/JP2020/016928
§ 371 (c)(1),
(2) Date: Oct. 15, 2021

(87) PCT Pub. No.: WO2020/213728
PCT Pub. Date: Oct. 22, 2020

(65) Prior Publication Data
US 2022/0322627 A1  Oct. 13, 2022

(30) Foreign Application Priority Data
Apr. 17, 2019 (JP) .................. 2019-078906

(51) Int. Cl.
*A01H 1/02* (2006.01)
*A01H 5/10* (2018.01)
*A01H 6/20* (2018.01)
*C12Q 1/6895* (2018.01)

(52) U.S. Cl.
CPC ............ *A01H 1/023* (2021.01); *A01H 5/10* (2013.01); *A01H 6/204* (2018.05); *C12Q 1/6895* (2013.01)

(58) Field of Classification Search
None
See application file for complete search history.

(56) References Cited

U.S. PATENT DOCUMENTS 5,650,559 A  7/1997  Akamatsu et al.

FOREIGN PATENT DOCUMENTS

| | | |
|---|---|---|
| CN | 1232608 A | 10/1999 |
| GB | 2478682 B | 10/2012 |
| JP | H07-31307 A | 2/1995 |
| JP | 2005-185102 A | 7/2005 |
| JP | 3964368 B2 | 8/2007 |
| JP | 5089764 B2 | 12/2012 |

OTHER PUBLICATIONS

Jeong et al Chlorosis of Ogura-CMS *Brassica rapa* is due to down-regulation of genes for chloroplast proteins J Plant Biotechnol 44 : 115-124 (Year: 2017).*
Hiroshi Yamagishi et. al., "Cytoplasmic male sterility in Brassicaceae crops"; Breeding Science 64; Year 2014; pp. 38-47 (total 10 pages).
Xi-Lin Hou, et al., "Creation of a New Germplasm of CMS Non-Heading Chinese Cabbage"; ISHS Acta Horticulturae 637; Year 2004; pp. 75-81 (total 7 pages).

* cited by examiner

*Primary Examiner* — Brent T Page
(74) *Attorney, Agent, or Firm* — Harness, Dickey & Pierce, P.L.C.

(57) ABSTRACT

A cytoplasmic male sterile *Brassica rapa* plant is provided having a growth ability equivalent to that of a *Brassica rapa* plant having a normal cytoplasm or a progeny of the cytoplasmic male sterile *Brassica rapa* plant. For example, it is possible to improve the deterioration of growth ability which has been observed in the conventional cytoplasmic male sterile *B. rapa* plants and provide a cytoplasmic male sterile *Brassica rapa* plant having an improved growth ability.

21 Claims, No Drawings
Specification includes a Sequence Listing.

CYTOPLASMIC MALE STERILE *BRASSICA RAPA* PLANT HAVING IMPROVED GROWTH ABILITY

CROSS-REFERENCE TO RELATED APPLICATIONS

This application is a U.S. National Phase application under 35 U.S.C. 371 of International Application No. PCT/JP2020/016928, filed on Apr. 17, 2020, which claims priority from prior Japanese Patent Application No. 2019-078906, filed on Apr. 17, 2019. The entire disclosures of the above applications are expressly incorporated by reference herein.

BACKGROUND OF THE INVENTION

Technical Field

The present invention relates to a cytoplasmic male sterile *Brassica rapa* plant having an improved growth ability.

Background Art

*Brassica rapa* belongs to the genus *Brassica* and the family Brassicaceae (commonly referred to as the mustard family), and is said to have originated in the Mediterranean region. *Brassica rapa* have been differentiated into subspecies having various morphological characteristics due to natural crossing, resulting in many vegetables such as Chinese cabbage, turnip, Japanese mustard spinach and pak choi (Non Patent Literature 1).

In general, commercial plant varieties include true-breeding varieties and first filial generation hybrid varieties (hereinafter referred to as "F1"), and F1 varieties are widespread among major crops. F1 varieties have great advantages such as vigorous growth due to heterosis, fast growth, and increased yield. Furthermore, F1 varieties can be expected to be improved in resistance to pests and environmental adaptability such as cold tolerance and heat tolerance due to the vigorous growth thereof. Moreover, since the genotypes of F1 varieties are heterozygous but individual plants have the same genotype, the individual plants show extremely high phenotypic uniformity. Therefore, the marketability of products from the F1 varieties is increased. Furthermore, since useful traits controlled by dominant genes can be accumulated in parents of F1 varieties, rapid variety development is possible.

Due to the above-mentioned advantages, F1 varieties have come to occupy the mainstream of cultivars in major crops.

In the production of seeds of F1 varieties, true-breeding self-fertilized (inbred) lines have been generally used as parents, and seed parents and pollen parents that have a large effect of heterosis are selected from testing F1 combinations. For seed parents it is necessary to use emasculation of flowers for preventing the occurrence of self-fertilization. However, manual emasculation requires a great deal of labor. Therefore, when a line having cytoplasmic male sterility (hereinafter referred to as "CMS"), which is genetically male-sterile, is used as the seed parent, manual emasculation becomes unnecessary and F1 seeds can be produced economically and in a large quantity. For the production of F1 seeds utilizing CMS, commercial production systems have been established for sunflower, sugar beet, potato, wheat, carrot, onion, bunching onion, cabbage, broccoli, cauliflower, daikon radish, Chinese cabbage and the like.

Among Brassicaceae family crops, the most utilized CMS is Ogura CMS, which has been used in *Raphanus sativus*, *Brassica oleracea*, *Brassica juncea*, *Brassica napus* and others. Ogura CMS was discovered in a daikon radish having an unknown variety name, and has been widely utilized for the development of F1 varieties of daikon radish. Furthermore, Ogura CMS was introduced into rapeseed (*Brassica napus*) by intergeneric crossing and recurrent backcrossing to obtain a male sterile line. However, the male sterile line initially had the drawback of showing chlorosis at low temperatures and could not be put into practical use. In order to overcome this chlorosis, protoplast fusion was carried out between Ogura CMS *B. napus* and *B. napus* having a normal cytoplasm. In a regenerated plant thus obtained, chloroplasts originated from daikon radish were replaced with chloroplasts originated from *B. napus*, and the plants grew normally even at low temperatures. Hence, in *B. napus* a practical CMS line has been developed by employing protoplast fusion (Non Patent Literature 2).

Later, protoplast fusion was also carried out between *B. oleracea* and *R. sativus*, and Ogura CMS *B. oleracea* plants that did not develop chlorosis were developed and were put into practical use in the development of F1 varieties such as broccoli and cabbage (Patent Literature 1).

As for the *B. rapa* plants, Ogura CMS *B. rapa* plants that do not develop chlorosis have been developed by recurrent backcrossing using the Ogura CMS *B. oleracea* plant disclosed in Patent Literature 1 as a seed parent and using a *B. rapa* plant as a pollen parent, and varieties of the plants have been established by Sakata Seed Corporation.

However, in the process of breeding, deterioration in growth ability was observed in many parent lines and F1 lines. Therefore, the growth ability of F1 seed produced utilizing existing CMS is generally deteriorated compared with F1 varieties produced utilizing self-incompatibility (hereinafter referred to as "SI"). Therefore, in *B. rapa* plants, the progress of the development of F1 utilizing CMS has not been advanced.

For example, for soft vegetables such as Japanese mustard spinach and pak choi, seeds are sown in stages, plants are then cultivated in a planned manner, and are then harvested all at once. Therefore, the equalization of maturity stage from sowing to harvesting is very important and is a characteristic property that directly correlates with the incomes for agricultural workers. In this regard, the problem of the deterioration in growth ability is so serious that the marketability is significantly reduced and the value as a variety is lost when harvesting period is delayed by 3 days. Even in Chinese cabbage, which requires a relatively long period for growth until harvesting, the growth ability is such an important property that a variety can be regarded as a different variety when the harvest time is shifted by about 5 days.

As mentioned above, in CMS-utilized F1 in *B. rapa* the prevention of the deterioration in growth of seedlings to fruits and vegetables is a very critical problem to address. For the above-mentioned reasons, the universal spread of CMS-utilized F1 in this species has been delayed. If this problem is overcome, the benefits of the above-mentioned CMS-utilized F1 can be fully obtained. Depending on the type of the line used, the decrease in growth ability can be small, so there are cases where the development of varieties succeeds while utilizing the heterosis of F1. However, the parent lines and combinations thereof which are available are limited and there is also limitation in breeding. Therefore, it has been keenly desired to develop Ogura CMS *B. rapa* plants that can be used universally.

In addition, in *B. rapa* plants, CMS can be introduced from an Ogura CMS *R. sativus* plant to a *B. rapa* by intergeneric crossing and recurrent backcrossing. Therefore, there was the case where an Ogura CMS *B. rapa* plant having nuclear replacement was produced by sexual crossing. However, as in the case of rapeseed, this plant has the drawback of showing chlorosis at low temperatures. In order to overcome this problem of chlorosis, asymmetric protoplast fusion was carried out between the Ogura CMS *B. rapa* plant nuclear-replaced by sexual crossing and a *B. rapa* plant having a normal cytoplasm to produce "new OguCMS" which is a new type of Ogura CMS *B. rapa* plant. "New OguCMS" does not develop chlorosis at low temperatures and has fully developed nectaries, and has characteristics such that the seed productivity of this plant is equivalent to those of maintainer (Patent Literature 2, Non Patent Literature 3).

However, in Patent Literature 2 and Non Patent Literature 3, the quantitative evaluation of growth ability of "new OguCMS" has not been made, and seeds of the CMS plant have not been deposited either. Therefore, it has been quite difficult to confirm the growth ability of "new OguCMS". In this regard, in the photograph shown in FIG. 1 in Non Patent Literature 3, the plant body of "new OguCMS" is apparently smaller than that of "parental CMS", and therefore the growth ability of "new OguCMS" is assumed to be poorer than a *B. rapa* plant having a normal cytoplasm. In addition, since both "Violet *Brassica campestris*" (also written as " 紫羅蘭油菜 " in Chinese characters) (see note 1) and "Ni hao fung", which the present inventors assumed to be "new OguCMS" plants, are all varieties of mini pak choi. From this fact, it is considered that "new OguCMS" has a poorer growth ability than that of a *B. rapa* plant having a normal cytoplasm.

(Note 1) The variety name " 紫罗兰油菜 " written in Chinese characters is also referred to as " 紫羅蘭油菜 ", hereinafter.

In the development of F1 varieties utilizing CMS, it is important that a cytoplasm that induces male sterility does not affect traits other than male sterility as much as possible. For example, in maize, a CMS cytoplasm having a T-type male sterile cytoplasm was bred. However, in 1970, the T-race of a southern leaf blight pathogen appeared. T-type male sterile cytoplasm was susceptible specifically to this pathogen, and therefore a lot of heavy damage was caused. For this reason, the utilization of a T-type male sterile cytoplasm was immediately discontinued, and there was no choice but to revert to the conventional emasculation method (detasseling) (Non Patent Literature 4).

In addition, CMS in *petunia* has been known for a long time, and S-pcf, which is a causative gene for CMS, is widely used as a subject of study. However, F1 varieties utilizing this CMS are rarely used at present, because the F1 varieties undergo delayed of flowering and arrested development of flower buds (Non Patent Literature 4).

As in these cases, even if CMS is discovered, when the CMS has a defective trait, the utilization of the CMS may be difficult or limited. Therefore, further development of a method for improving the CMS and the provision of an improved CMS is still desired.

CITATION LIST

Patent Literature

PTL 1: JP 7-31307 A
PTL 2: CN 1232608 A
PTL 3: JP 3964368 B2
PTL 4: JP 5089764 B2

Non Patent Literature

NPL 1: Keita Suwabe (2012) Breeding Research (Ikushugaku kenkyu) 14:114-120
NPL 2: Hiroshi Yamagishi and Shripad R. Bhat (2014) Breeding Science 64:38-47 "Cytoplasmic male sterility in Brassicaceae crops"
NPL 3: Xi-Lin Hou, Shou-Chun Cao, Yu-Ke He (2004) ISHS Acta Horticulturae 637:75-81 "Creation of a New Germplasm of CMS Non-Heading Chinese Cabbage"
NPL 4: Cytoplasmic Male Sterility and Breeding Technique, 1985, published by C. M. C. Publishing CO., LTD.

SUMMARY OF THE INVENTION

Technical Problem

In existing Ogura CMS *B. rapa* plants, the compatibility between the nuclear genome and mitochondrial genome is insufficient. Therefore, the existing Ogura CMS *B. rapa* plants have the problem that the growth ability is deteriorated compared with a *B. rapa* plant having a normal cytoplasm.

In view of the above-mentioned problems of the deterioration in growth ability in the existing Ogura CMS *B. rapa* plants, the object of the present invention is to provide an Ogura CMS *B. rapa* plant which does not undergo the deterioration in growth ability and also provide a method for producing F1 seeds of a *B. rapa* plant which does not undergo the deterioration in growth ability utilizing the Ogura CMS *B. rapa* plant.

Solution to Problem

The present inventors have now made extensive and intensive studies. As a result, it is found that it becomes possible to improve the mitochondrial genome by carrying out asymmetric protoplast fusion using an existing Ogura CMS *B. rapa* plant as a cytoplasm donor parent and using a *B. rapa* interspecific hybrid plant having a high regeneration ability and having a normal cytoplasm as a cytoplasm acceptor parent, and therefore it becomes possible to produce an Ogura CMS *B. rapa* plant that does not undergo the deterioration in growth ability and to produce an Ogura CMS *B. rapa* plant having an improved growth ability using the above-mentioned Ogura CMS *B. rapa* plant.

The present invention has been made on the basis of these findings. That is, according to the present invention, the following inventions are provided.

<1> A cytoplasmic male sterile *Brassica rapa* plant having a growth ability equivalent to that of a *Brassica rapa* plant having normal cytoplasm, or a progeny of the cytoplasmic male sterile *Brassica rapa* plant.

<2> The cytoplasmic male sterile *Brassica rapa* plant or the progeny thereof according to <1>, wherein the cytoplasmic male sterile *Brassica rapa* plant or the progeny thereof has, in the mitochondrial genome thereof, DNA molecules respectively derived from a mitochondrial genome of a *Raphanus sativus* plant, a mitochondrial genome of a *Brassica oleracea* plant and a mitochondrial genome of a *Brassica rapa* plant.

<3> The cytoplasmic male sterile *Brassica rapa* plant or the progeny thereof according to <1> or <2>, wherein the cytoplasmic male sterile *Brassica rapa* plant or the progeny thereof is produced by carrying out asymmetric protoplast fusion using a *Brassica rapa* interspecific hybrid plant having a normal cytoplasm as a cytoplasm acceptor parent.

<4> The cytoplasmic male sterile *Brassica rapa* plant or the progeny thereof according to any one of <1> to <3>, wherein the cytoplasmic male sterile *Brassica rapa* plant or the progeny thereof is produced by carrying out asymmetric protoplast fusion using a cytoplasmic male sterile *Brassica* plant having a cytoplasmic male sterility gene originated from a *Raphanus sativus* plant as a cytoplasm donor parent.

<5> The cytoplasmic male sterile *Brassica rapa* plant or the progeny thereof according to any one of <1> to <3>, wherein the cytoplasmic male sterile *Brassica rapa* plant or the progeny thereof is produced by carrying out asymmetric protoplast fusion using a cytoplasmic male sterile *Brassica* plant originated from a cytoplasmic male sterile *Brassica oleracea* plant as a cytoplasm donor parent.

<6> The cytoplasmic male sterile *Brassica rapa* plant or the progeny thereof according to any one of <1> to <3>, wherein the cytoplasmic male sterile *Brassica rapa* plant or the progeny thereof is produced by carrying out asymmetric protoplast fusion using a cytoplasmic male sterile *Brassica rapa* plant originated from a cytoplasmic male sterile *Brassica oleracea* plant as a cytoplasm donor parent.

<7> The cytoplasmic male sterile *Brassica rapa* plant or the progeny thereof according to any one of <1> to <4>, wherein the cytoplasmic male sterile *Brassica rapa* plant or the progeny thereof is produced by carrying out asymmetric protoplast fusion using an existing-cytoplasmic-male-sterile *Brassica* plant as a cytoplasm donor parent and using a *Brassica rapa* interspecific hybrid plant having a normal cytoplasm as a cytoplasm acceptor parent.

<8> The cytoplasmic male sterile *Brassica rapa* plant or the progeny thereof according to any one of <3> to <7>, wherein the interspecific hybrid plant is originated from a *Brassica oleracea* plant and a *Brassica rapa* plant.

<9> The interspecific hybrid plant according to any one of <3> to <8>, wherein the interspecific hybrid plant has a high regeneration ability.

<10> The cytoplasmic male sterile *Brassica rapa* plant or the progeny thereof according to <7>, wherein the existing-cytoplasmic-male-sterile *Brassica* plant is an existing-cytoplasmic-male-sterile *Brassica rapa* plant.

<11> The cytoplasmic male sterile *Brassica rapa* plant or the progeny thereof according to <7>, wherein the existing-cytoplasmic-male-sterile *Brassica* plant is originated from a cytoplasmic male sterile *Brassica oleracea* plant.

<12> The cytoplasmic male sterile *Brassica rapa* plant or the progeny thereof according to any one of <4> to <11>, wherein the cytoplasm donor parent has a cytoplasmic male sterility gene orf138.

<13> A cytoplasmic male sterile *Brassica rapa* plant having in the mitochondrial genome thereof, DNA molecules respectively originated from a mitochondrial genome of a *Raphanus sativus* plant, a mitochondrial genome of a *Brassica oleracea* plant and a mitochondrial genome of a *Brassica rapa* plant, or a progeny of the cytoplasmic male sterile *Brassica rapa* plant, the cytoplasmic male sterile *Brassica rapa* plant or the progeny thereof being able to be produced by carrying out asymmetric protoplast fusion using a *Brassica rapa* interspecific hybrid plant having a normal cytoplasm as a cytoplasm acceptor parent.

<14> The cytoplasmic male sterile *Brassica rapa* plant or the progeny thereof according to any one of <1> to <13>, wherein the cytoplasmic male sterile *Brassica rapa* plant or the progeny thereof contains a mitochondrial genome originated from a plant identified by Accession No. FERM BP-22371 or Accession No. FERM BP-22372.

<15> The cytoplasmic male sterile *Brassica rapa* plant or the progeny thereof according to any one of <1> to <14>, wherein at least one of mitochondrial DNA molecules respectively identified by mitochondrial genome markers BrMt-13K, BrMt-23K, BrMt-74K, BrMt-120K, BrMt-149K and BrMt-185K is of a *Brassica rapa* type.

<16> The *Brassica rapa* plant or the progeny thereof according to any one of <1> to <14>, wherein at least one of mitochondrial DNA molecules respectively identified by mitochondrial genome markers BrMt-119K, BrMt-133K, BrMt-139K, BrMt-171K and BrMt-208K is of a *Brassica oleracea* type.

<17> The *Brassica rapa* plant or the progeny thereof according to any one of <1> to <14>, wherein each of mitochondrial DNA molecules respectively identified by mitochondrial genome markers BrMt-13K, BrMt-16K, BrMt-23K, BrMt-28K, BrMt-43K, BrMt-58K, BrMt-63K, BrMt-70K, BrMt-74K, BrMt-88K, BrMt-100K, BrMt-111K, BrMt-120K, BrMt-141K, BrMt-149K, BrMt-157K, BrMt-161K, BrMt-185K, BrMt-199K, BrMt-213K and BrMt-215K is of a *Brassica rapa* type and each of mitochondrial DNA respectively identified by mitochondrial genome markers BrMt-3K, BrMt-4K, BrMt-36K, BrMt-65K, BrMt-80K, BrMt-94K, BrMt-119K, BrMt-133K, BrMt-139K, BrMt-171K and BrMt-208K is of a *Brassica oleracea* type.

<18> A cytoplasmic male sterile *Brassica rapa* plant having a mitochondrial genome of a plant identified by Accession No. FERM BP-22371 or Accession No. FERM BP-22372, or a progeny of the cytoplasmic male sterile *Brassica rapa* plant.

<19> A cytoplasmic male sterile *Brassica rapa* plant identified by Accession No. FERM BP-22371 or Accession No. FERM BP-22372, or a progeny of the cytoplasmic male sterile *Brassica rapa* plant.

<20> The cytoplasmic male sterile *Brassica rapa* plant or the progeny thereof according to any one of <1> to <19>, wherein the cytoplasmic male sterile *Brassica rapa* plant or the progeny thereof is produced by carrying out asymmetric protoplast fusion using a cytoplasmic male sterile *Brassica rapa* plant having a mitochondrial genome of a plant identified by Accession No. FERM BP-22371 or Accession No. FERM BP-22372 as a cytoplasm donor parent and a *Brassica rapa* interspecific hybrid plant having a normal cytoplasm is used as a cytoplasm acceptor parent.

<21> A part of a plant body of a cytoplasmic male sterile *Brassica rapa* plant or a progeny thereof as recited in any one of <1> to <20>.

<22> A seed of a cytoplasmic male sterile *Brassica rapa* plant or a progeny thereof as recited on any one of <1> to <20>.

<23> A mitochondrial genome contained in a cytoplasmic male sterile *Brassica rapa* plant or a progeny thereof as recited in any one of <1> to <20>, a part of a plant body as recited in <21> or a seed as recited in <22>.

<24> A method for producing a cytoplasmic male sterile *Brassica rapa* plant having a growth ability equivalent to that of a *Brassica rapa* plant having a normal cytoplasm or a progeny of the cytoplasmic male sterile *Brassica rapa* plant, the method comprising carrying out asymmetric protoplast fusion using an existing-cytoplasmic-male-sterile *Brassica* plant as a cytoplasm donor parent and a *Brassica rapa* plant having a normal cytoplasm as a cytoplasm acceptor parent.

<25> The production method according to <24>, wherein the *Brassica rapa* plant having a normal cytoplasm is an interspecific hybrid plant of a *Brassica rapa* plant or a plant derived from the interspecific hybrid plant.

<26> A method for producing a first filial generation seed, comprising the steps of: crossing as a seed parent a cytoplasmic male sterile *Brassica rapa* plant or a progeny thereof as recited in any one of <1> to <20> and as a pollen parent a *Brassica rapa* plant capable of being crossed with said plant; and collecting a first filial generation seed from the seed parent after the crossing.

<27> A first filial generation seed produced by a method as recited in <26>, a first filial generation plant grown from the seed or a progeny thereof, or a part of a plant body of the first filial generation plant or the progeny thereof.

<28> A method for producing a *Brassica rapa* plant exhibiting cytoplasmic male sterility, the method comprising carrying out the recurrent backcrossing of an arbitrary *Brassica rapa* plant to a cytoplasmic male sterile *Brassica rapa* plant or a progeny thereof as recited in any one of <1> to <20> to achieve cytoplasmic replacement.

Effects of the Invention

According to the present invention, it is possible to provide a cytoplasmic male sterile *Brassica rapa* plant having an improved growth ability, particularly an Ogura CMS *B. rapa* plant having an improved growth ability. By using the cytoplasmic male sterile *B. rapa* plant having an improved growth ability according to the present invention as a seed parent and using a *B. rapa* plant having a normal cytoplasm as a pollen parent for the production of F1 seeds of the *B rapa* plant, it becomes possible to efficiently produce F1 seeds of a *B. rapa* plant which does not undergo the deterioration in growth ability.

DETAILED DESCRIPTION OF THE INVENTION

Hereinbelow, the present invention will be described in detail.

Cytoplasmic male sterile *Brassica rapa* plant having improved growth ability and progeny thereof The present invention relates to a cytoplasmic male sterile *B. rapa* plant having an improved growth ability compared with those of existing-cytoplasmic-male-sterile *B. rapa* plants or a progeny of the cytoplasmic male sterile *Brassica rapa* plant. As mentioned above, the cytoplasmic male sterile *B. rapa* plant or the progeny thereof can also be described as "a cytoplasmic male sterile *B. rapa* plant having a growth ability equivalent to that of a *B. rapa* plant having a normal cytoplasm or a progeny of the cytoplasmic male sterile *B. rapa* plant".

In the present invention, the term "normal cytoplasm" is typically used in the meaning that the cytoplasm does not exhibit sterility and is normal in contrast to a plant cytoplasm exhibiting male sterility, i.e., a male sterile cytoplasm.

In the wording "a growth ability equivalent to that of a *B. rapa* plant having a normal cytoplasm", the term "equivalent" refers to the case where, when a growth ability is determined in terms of a value obtained by weighing an aerial part of a plant body, a weighed value for a plant of interest falls within a range where the value varies within 25% (preferably 20%, more preferably 15%, still more preferably 10%) of a weighed value for *B. rapa* plant having a normal cytoplasm. For example, in the case where the weighed value for a plant of interest is 90% of a weighed value of an aerial part of a normal plant of "a *B. rapa* plant having a normal cytoplasm", the above-mentioned variation corresponds to 10%. The term "equivalent" does not exclude the case where the growth ability of a plant exceeds that of a "*B. rapa* plant having a normal cytoplasm".

The term "progeny" as used herein includes a progeny developed using a *B. rapa* plant having a normal cytoplasm, as well as a hybrid produced by crossing the cytoplasmic male sterile *B. rapa* plant having an improved growth ability according to the present invention with a *B. rapa* plant capable of being crossed with the plant. Therefore, the term "progeny" also includes, for example, a plant produced by crossing the cytoplasmic male sterile *B. rapa* plant having an improved growth ability according to the present invention, which is used as a seed parent (i.e., a female parent), with a *B. rapa* plant capable of being crossed with the plant, which is used as a pollen parent (i.e., a male parent). Furthermore, the term "progeny" also includes, for example, a plant produced by the protoplast fusion of the cytoplasmic male sterile *B. rapa* plant having an improved growth ability according to the present invention with a plant capable of being fused with the *B. rapa* plant, or an interspecific/intergeneric hybrid plant between these *B. rapa* plants.

The wording "*B. rapa* plant" is preferably pak choi (*B. rapa* var. *chinensis*), turnip (*B. rapa* var. *rapa*), potherb mustard Mizuna (*B. rapa* var. *laciniifolia*), Chinese cabbage (*B. rapa* var. *pekinensis*), Japanese mustard spinach (*B. rapa* var. *perviridis*), tatsoi (*B. rapa* var. *narinosa*), or an interspecific/intergeneric hybrid plant between any one of the aforementioned plants and a closely related species thereof.

According to a preferred aspect of the present invention, the cytoplasmic male sterile *B. rapa* plant having an improved growth ability of the present invention or a progeny thereof has, in the mitochondrial genome thereof, orf138 gene which is a cytoplasmic male sterility gene originated from a *Raphanus sativus* plant, more preferably has, in the mitochondrial genome thereof, DNA molecules respectively originated from a mitochondrial genome of a *Raphanus sativus* plant, a mitochondrial genome of a *Brassica oleracea* plant and a mitochondrial genome of a *Brassica rapa* plant, still more preferably has orf138 gene originated from a *R. sativus* plant and recombinant mitochondrial genomes respectively originated from a *B. oleracea* plant and a *B. rapa* plant.

The term "asymmetric protoplast fusion" as used herein refers to a matter that a nuclear genome of one of several isolated protoplasts that are to be used for protoplast fusion is disrupted prior to the fusion and then the protoplast fusion is carried out using the disrupted nuclear genome. In the asymmetric protoplast fusion, a cell in which a nuclear genome is disrupted upon fusion and of which a cytoplasm is donated to a fused cell through protoplast fusion is referred to as a "cytoplasm donor parent". A cell in which a nuclear genome is maintained without being disrupted upon fusion and which receives the cytoplasm from the cytoplasm donor parent upon the fusion is referred to as a "cytoplasm acceptor parent".

In the production of the cytoplasmic male sterile *B. rapa* plant having an improved growth ability according to the present invention, it is desirable to use a *B. rapa* interspecific hybrid plant having a normal cytoplasm as a cytoplasm acceptor parent in the asymmetric protoplast fusion. Therefore, according to a preferred aspect of the present invention, the cytoplasmic male sterile *B. rapa* plant having an improved growth ability of the present invention can be produced by carrying out asymmetric protoplast fusion using an existing-cytoplasmic-male-sterile *B. rapa* plant as a cytoplasm donor parent and using a *B. rapa* interspecific hybrid plant having a normal cytoplasm as a cytoplasm acceptor parent.

The term "existing-cytoplasmic-male-sterile *B. rapa* plant" as used herein refers to a cytoplasmic male sterile *B. rapa* plant of which the growth ability is not improved yet by the present invention. In the present invention, the term "existing-cytoplasmic-male-sterile *B. rapa* plant" preferably refers to a cytoplasmic male sterile *B. rapa* plant in which there is a room for improving the growth ability thereof, i.e., a cytoplasmic male sterile *B. rapa* plant having a poorer growth ability compared with a *B. rapa* plant having a normal cytoplasm.

According to a preferred aspect of the present invention, the existing-cytoplasmic-male-sterile *Brassica rapa* plant is a cytoplasmic male sterile *Brassica rapa* plant originated from a cytoplasmic male sterile *Brassica oleracea* plant. The cytoplasmic male sterile *Brassica oleracea* plant can be developed with reference to JP 07-031307 A, and one typical example thereof is a CMS line "Cabbage MS-2" (JP 07-031307 A) which has been developed by Sakata Seed Corporation and has been used in a *B. oleracea* crop. The cytoplasm of "Cabbage MS-2" has been used in commercially available broccoli varies "Grandome", "Pixel" and the like and is easily available.

The cytoplasmic male sterile *Brassica* plant having a cytoplasmic male sterility gene originated from *Raphanus sativus* is typically one having Ogura CMS gene, as mentioned above.

According to one preferred aspect of the present invention, in the *Brassica rapa* plant of the present invention or a progeny thereof, at least any one of mitochondrial DNA molecules identified by mitochondrial genome markers BrMt-13K, BrMt-23K, BrMt-74K, BrMt-120K, BrMt-149K and BrMt-185K is of a *Brassica rapa* type. The wording "at least any one" as used herein means more preferably "at least any two", still more preferably "at least any three", furthermore preferably "at least any four". According to a more preferred aspect, in the *Brassica rapa* plant of the present invention or a progeny thereof, each of the mitochondrial DNA molecules identified by mitochondrial genome markers BrMt-13K, BrMt-23K, BrMt-74K, BrMt-120K, BrMt-149K and BrMt-185K is of a *Brassica rapa* type.

According to one preferred aspect of the present invention, in the *Brassica rapa* plant of the present invention or a progeny thereof, at least any one of mitochondrial DNA molecules identified by mitochondrial genome markers BrMt-119K, BrMt-133K, BrMt-139K, BrMt-171K and BrMt-208K is of a *Brassica oleracea* type. The wording "at least any one" as used herein means more preferably "at least any two", still more preferably "at least any three", furthermore preferably "at least any four". According to a more preferred aspect, in the *Brassica rapa* plant of the present invention or a progeny thereof, each of the mitochondrial DNA molecules identified by mitochondrial genome markers BrMt-119K, BrMt-133K, BrMt-139K, BrMt-171K and BrMt-208K is of a *Brassica oleracea* type.

According to one preferred aspect of the present invention, in the *Brassica rapa* plant of the present invention or a progeny thereof, at least any one of the mitochondrial DNA molecules identified by mitochondrial genome markers BrMt-13K, BrMt-16K, BrMt-23K, BrMt-28K, BrMt-43K, BrMt-58K, BrMt-63K, BrMt-70K, BrMt-74K, BrMt-88K, BrMt-100K, BrMt-111K, BrMt-120K, BrMt-141K, BrMt-149K, BrMt-157K, BrMt-161K, BrMt-185K, BrMt-199K, BrMt-213K and BrMt-215K is of a *Brassica rapa* type, and at least any one of the mitochondrial DNA identified by mitochondrial genome markers BrMt-3K, BrMt-4K, BrMt-36K, BrMt-65K, BrMt-80K, BrMt-94K, BrMt-119K, BrMt-133K, BrMt-139K, BrMt-171K and BrMt-208K is of a *Brassica oleracea* type. The wording "at least any one" as used herein means more preferably "at least any two", still more preferably "at least any three", furthermore preferably "at least any four".

According to one more preferred aspect of the present invention, in the *Brassica rapa* plant of the present invention or a progeny thereof, each of the mitochondrial DNA molecules identified by mitochondrial genome markers BrMt-13K, BrMt-16K, BrMt-23K, BrMt-28K, BrMt-43K, BrMt-58K, BrMt-63K, BrMt-70K, BrMt-74K, BrMt-88K, BrMt-100K, BrMt-111K, BrMt-120K, BrMt-141K, BrMt-149K, BrMt-157K, BrMt-161K, BrMt-185K, BrMt-199K, BrMt-213K and BrMt-215K is or a *Brassica rapa* type, and each of the mitochondrial DNA identified by mitochondrial genome markers BrMt-3K, BrMt-4K, BrMt-36K, BrMt-65K, BrMt-80K, BrMt-94K, BrMt-119K, BrMt-133K, BrMt-139K, BrMt-171K and BrMt-208K is of a *Brassica oleracea* type.

According to a more preferred aspect of the present invention, the cytoplasmic male sterile *B. rapa* plant having an improved growth ability according to the present invention or a progeny thereof is a *B. rapa* plant having the mitochondrial genome of the same plant as Accession No. FERM BP-22371 or FERM BP-22372 (mentioned below) or a progeny thereof, is more preferably a *B. rapa* plant that is the same as Accession No. FERM BP-22371 or FERM BP-22372 or a progeny thereof.

The term "a part of a plant body" of the cytoplasmic male sterile *B. rapa* plant having an improved growth ability or a progeny thereof as used herein includes one or more cells of the plant body or a cytoplasm composed of one or more cells of the plant body, and specifically refers to an organ (e.g., a flower, a leaf, a stem, a root) or a tissue, or a cell (including a protoplast prepared from cells) or a cytoplasm from the organ or the tissue, or a mass of the cells or the cytoplasms.

Method for Producing Cytoplasmic Male Sterile *B. rapa* Plant Having Improved Growth Ability The cytoplasmic male sterile *B. rapa* plant having an improved growth ability according to the present invention can be produced, for example, in accordance with the following procedure.

(1) Production of a cytoplasm acceptor parent having a high regeneration ability and a normal cytoplasm.

(2) Preparation of a protoplast.

(i) Isolation of a protoplast of a *B. rapa* interspecific hybrid plant having a normal cytoplasm.

(ii) Isolation of a protoplast of an existing-cytoplasmic-male-sterile *B. rapa* plant.

(3) Fusion treatment of the protoplasts.

(4) Culture of a fused hybrid cell.

(5) Selection of a cytoplasmic hybrid having cytoplasmic male sterility.

(6) Regeneration of a plant body from a callus.

(7) Acquisition of a progeny and selection of a high-quality line.

In the description, the term "production method" can also be referred to as the term "development method". The terms "development" and "production" can be used interchangeably with each other.

More specifically, these steps are as follows.

(1) Production of a Cytoplasm Acceptor Parent Having a High Regeneration Ability and a Normal Cytoplasm.

As mentioned above, in the development of an F1 variety utilizing CMS, it is important that the cytoplasm causing male sterility does affect a trait other than male sterility as much as possible. In the case where a cytoplasm hybrid is produced utilizing an asymmetric protoplast fusion technique, the recombination of a mitochondrial genome occurs randomly, and therefore the probability of acquisition of a recombinant mitochondrion that can maintain the male sterility thereof without any defective trait is low. In this case, it is needed to produce many cytoplasm hybrid individuals and select a high-quality individual from the cytoplasm hybrid individuals.

However, with respect to a *B. rapa* plant, the regeneration of a plant body from fused cell produced by asymmetric protoplast fusion is more difficult compared with a *B. oleracea* plant and a *B. napus* plant which are the same *Brassica* plants as the *B. rapa* plant. Therefore, any efficient method for producing a cytoplasmic hybrid of a *B. rapa* plant has not been reported yet. Consequently, it is essential to develop a method for producing a great number of cytoplasm hybrids efficiently.

The term "cytoplasmic hybrid" as used herein refers to a plant in which the cytoplasm is in a hybrid state, such as a plant produced by carrying out protoplast fusion (preferably asymmetric protoplast fusion).

In a mustard family plant, when asymmetric protoplast fusion utilizing a radioactive ray such as soft X-ray is carried out, some of fragmented nuclear genomes of a cytoplasm donor parent are often introduced, and therefore the division of a fused cell or the regeneration of a plant body from the fused cell may be often difficult. Therefore, in order to produce the cytoplasm hybrid efficiently, it is very important to increase the regeneration ability of a cytoplasm acceptor parent as high as possible.

Among mustard family plants, a *B. oleracea* plant is known to have a high regeneration ability from a cultured cell. In contrast, a *B. rapa* plant has a poor regeneration ability, and examples of the success of regeneration of a plant body from a cultured cell are limited in specific varieties. Therefore, in order to increase the efficiency of the production of a cytoplasm hybrid, it is desirable to firstly produce an interspecific hybrid plant using a *B. rapa* plant having a normal cytoplasm as a seed parent and using a *B. oleracea* plant as a pollen parent to thereby produce an interspecific hybrid plant between the *B. rapa* plant that has a high regeneration ability with the *B. oleracea* plant, and then use the interspecific hybrid plant as a cytoplasm acceptor parent.

Hereinbelow, the term "interspecific hybrid plant between *B. rapa* and *B. oleracea* having a high regeneration ability" is also referred to as a "*B. rapa* interspecific hybrid plant". The *B. rapa* interspecific hybrid plant is produced using a *B. rapa* plant having a normal cytoplasm as a seed parent, and the cytoplasm is maternally inherited. As a result, the *B. rapa* interspecific hybrid plant has the same cytoplasm as that of the *B. rapa* having a normal cytoplasm and is improved in the regeneration ability thereof. Therefore, the *B. rapa* interspecific hybrid plant has desirable properties for use as a cytoplasm acceptor parent.

In this regard, the wording "high regeneration ability" refers to a high ability to be regenerated from a callus of cells into a plant body, in which the regeneration ratio (i.e., (the number of regenerated calluses)/(the number of calluses bedded on the regeneration culture medium)) 1 month after the bedding of the callus on a regeneration culture medium is 30% or more, more preferably 50% or more.

Still more preferably, backcrossing is carried out using an amphidiploid produced by artificially ploidizing the *B. rapa* interspecific hybrid plant as a seed parent and using a *B. rapa* plant having a normal cytoplasm as a pollen parent, a resultant progeny is subjected to tissue culture, and an individual having a high regeneration ability is selected, thereby producing a triploid *B. rapa* interspecific hybrid plant having a high regeneration ability. In this manner, by repeating the recurrent backcrossing using a *B. rapa* plant having a normal cytoplasm as a pollen parent and the selection of an individual having a high regeneration ability by tissue culture, it is possible to produce a diploid *B. rapa* interspecific hybrid plant having a nuclear genome close to that of *B. rapa*. The female fertility increases as the polyploidity comes close to a diploid. Therefore, it is desirable to use these *B. rapa* interspecific hybrid plants as cytoplasm acceptor parents.

(2) Preparation of a Protoplast.

(i) Isolation of a Protoplast of a *B. rapa* Interspecific Hybrid Plant Having a Normal Cytoplasm In the present invention, the *B. rapa* plant to be used as a cytoplasm acceptor parent is the *B. rapa* interspecific hybrid plant mentioned in section (1) above, more preferably a *B. rapa* interspecific hybrid plant that is produced by the backcrossking of *B. rapa* with the aforementioned *B. rapa* interspecific hybrid plant and is then bred.

As the cell tissue to be used for producing the protoplast, it is desirable to provide a mesophyll tissue that has a high yielding ability and a high division activity. Alternatively, another tissue, e.g., a hypocotyl, a stem and a callus, may also be used as a material for the cell tissue.

The method for isolating the protoplast may be a known method that has been used commonly in the art (e.g., the method described in Matsumoto, E, Plant cell reports, 1991. vol 9 (10) or the like), and is not particularly limited. Hereinbelow, specific examples of the procedure will be described. However, the present invention is not limited to these examples.

Firstly, a cell tissue of a *B. rapa* plant is finely cut and is then enzymatically treated using an enzyme solution for protoplast isolation use to isolate a protoplast. The solution is an inorganic salt buffer mainly containing a cell wall degradation enzyme and an osmotic pressure regulator. The cell wall degradation enzyme is not particularly limited, as long as the cell wall degradation enzyme can be used for the degradation of a cell wall of a plant. Examples the cell wall degradation enzyme include a cellulase, a hemicellulase and a pectinase. In the present invention, a combination of Cellulase Y-C and Macerozyme R-10 is preferred.

As the osmotic pressure regulator, a common sugar alcohol, e.g., mannitol, sorbitol and glucose, can be used. Among these sugar alcohols, mannitol is preferred, and mannitol at a concentration of 0.3 M to 0.7 M is particularly preferred. Furthermore, it is desirable to add an inorganic salt to the enzyme solution for the purpose of stabilizing a membrane of the protoplast. For example, it is preferred to add a CPW salt (Cocking and Peberdy, 1974) having the composition shown in Table 1. The enzymatic treatment is preferably carried out by statically treating at 25 to 30° C. for 8 to 20 hours.

TABLE 1

| Composition of CPW salt solution | |
| --- | --- |
| $KH_2PO_4$ | 27.2 mg/l |
| $KNO_3$ | 101.0 mg/l |
| $CaCl_2 \cdot 2H_2O$ | 1,480.0 mg/l |
| $MgSO_4$ | 246.0 mg/l |
| KI | 0.16 mg/l |
| $CuSO_4 \cdot 5H_2O$ | 0.025. mg/l |
| Mannitol | 0.6M |
| pH | 5.8 |

The protoplast isolated by the enzymatic treatment is filtrated through a nylon mesh having a pore diameter of 30 to 100 μm, then a filtrate is centrifuged, the protoplast is collected and the enzyme solution is discarded. Subsequently, the protoplast is suspended in a wash solution to wash the protoplast. As the wash solution, one prepared by adding a sugar alcohol as an osmotic pressure regulator to a commonly used CPW salt solution can be used.

Subsequently, it is desirable to carry out an inactivation treatment for the purpose of preventing the division of the B. rapa interspecific hybrid plant protoplast alone. The inactivation treatment can be carried out by suspending the protoplast in a CPW salt solution having an iodo compound, e.g., iodoacetic acid and iodoacetamide, dissolved therein. In the present invention, it is preferred to suspend the protoplast in a CPW solution prepared so as to contain iodoacetamide at a concentration of 5 mM to 30 mM and then carry out the treatment for 5 to 20 minutes.

Subsequently, it is preferred to repeat a washing operation with a CPW salt solution using a centrifuge machine 1 to 3 times. The suspension of the protoplast is contaminated with vessels and cell fragments. Therefore, it is preferred to further purify the suspension by a density gradient centrifugation method or the like.

Examples of the reagent to be used for the purification include a sugar and a synthetic colloid. In the present invention, it is preferred to use a sucrose solution, and it is particularly preferred to use a sucrose solution having a concentration of 15% to 20%. After the purification of the protoplast, the cell density is measured using a hemocytometer, and the volume of the solution is adjusted with a CPW salt solution in such a manner that the cell density can have a value suitable for protoplast fusion. The cell density of the protoplast is preferably $1 \times 10^5$ to $1 \times 10^7$ cells/ml, and a CPW salt solution is preferably used for the adjustment of the volume of the solution.

(ii) Isolation of a Protoplast of an Existing-Cytoplasmic-Male-Sterile B. rapa Plant.

The existing-cytoplasmic-male-sterile B. rapa plant to be used as a cytoplasm donor parent is not particularly limited. It is desirable to use a CMS line "Cabbage MS-2" (JP 07-031307 A) which has been developed by Sakata Seed Corporation and has been used as a B. oleracea crop. The cytoplasm of "Cabbage MS-2" has been used in commercially available broccoli varies "Grandome", "Pixel" and the like and is easily available. The cytoplasm of "Cabbage MS-2" can be used directly. However, it is more desirable to carry out nuclear replacement by the conventional recurrent backcrossing of a B. rapa plant to produce a cytoplasmic male sterile B. rapa plant and use the cytoplasmic male sterile B. rapa plant.

The isolation of a protoplast of the existing-cytoplasmic-male-sterile plant can be carried out in accordance with, for example, the same method as the above-mentioned method employed for the isolation of a protoplast of the B. rapa interspecific hybrid plant.

It is desirable to inactivate the nucleus of the isolated protoplast of the existing-cytoplasmic-male-sterile B. rapa plant in by a radioactive ray treatment upon use. Examples of the radioactive ray to be emitted for the radioactive ray treatment include X-ray, γ-ray, and ultraviolet ray. The radioactive ray is not particularly limited, as long as the nucleus can be destroyed. The exposure radiation dose is preferably as small as possible within such a range that the nucleus can be destroyed. For example, in the present invention, in the case of the irradiation with soft X-ray, the exposure radiation dose is preferably 100 Gy to 900 Gy.

(3) Fusion Treatment of the Protoplasts.

Subsequently, the protoplasts of both of the species which have been obtained in the above-mentioned steps are mixed together to carry out protoplast fusion.

Examples of the fusion method include, but are not particularly limited to, conventional methods, such as a known electrical fusion method (Planta, 151, 26-32, 1981), a PEG (polyethylene glycol) method (Planta, 120, 215-227, 1974) and a dextran method (Jap. J. Genet., 50, 235, 1975). In the present invention, it is preferred to employ a PEG method.

(4) Culture of a Fused Hybrid Cell.

The cell obtained by the fusion treatment is preferably cultured in a culture medium that is suitable for the culture of a protoplast originated from a B. rapa interspecific hybrid plant. The method for culturing a protoplast originated from an interspecific hybrid plant between B. rapa and B. oleracea having a high regeneration ability is not particularly limited, and is appropriately modified on the basis of a method for culturing a protoplast of a Brassica plant. In the present invention, it is preferred to use a half-strength MS medium in which the concentration of $NH_4NO_3$ is reduced to 200 mg/l as a basal medium and is appropriately supplemented with a plant growth regulating substance, various additives and the like upon use.

(5) Selection of a Cytoplasmic Hybrid Having Cytoplasmic Male Sterility

The fused cell is cultured. At the stage where cell division starts and a callus can be visually confirmed, the callus is transplanted into a callus proliferation medium. As the callus proliferation medium, a conventional one can be used. For example, an MS medium containing 1.0 to 5.0 mg/l of NAA and 0.1 to 3.0 mg/l of 4-CPPU can be used preferably, although reactivity may vary depending on the genotype of a plant that is used as a material or the condition of the callus.

As the causative gene for the cytoplasmic male sterility of Ogura CMS, orf138 occurring in a mitochondrial genome can be identified by PCR marker. Therefore, in order to select an individual having cytoplasmic male sterility from the resultant calluses, it is preferred to extract DNA from proliferated calluses by the above-mentioned procedure and is then detected by a PCR method using a marker capable of specifically proliferating orf138.

(6) Regeneration of a Plant Body from a Callus.

The thus-obtained callus having orf138 is transplanted into a regeneration medium to cause the regenerate of a plant body.

As the regeneration medium, a conventional one can be used. For example, an MS medium supplemented with 0.1 to 1.0 mg/l of NAA and 0.1 to 1.0 mg/l of 4-CPPU can be used preferably, although reactivity may vary depending on the genotype of a plant that is used as a material or the condition of the callus.

A regenerated shoot is transplanted into an MS medium supplemented with 3% of sucrose and 0.8% of agar and the like to cause the rooting of the shoot, thereby regenerating a plant body. The regenerated plant body is acclimated and is then grown in a greenhouse.

In the asymmetric protoplast fusion of a mustard family plant, generally a nucleus in a cytoplasm donor parent is destructed by a radioactive ray treatment. In this case, however, the destruction of a nuclear genome cannot be achieved completely, and a part of the genome may be often incorporated in the cytoplasm acceptor parent. Furthermore, because a plurality of protoplasts originated from the cytoplasm donor parent or a plurality of protoplasts originated from the cytoplasm acceptor parent may be fused upon the asymmetric protoplast fusion, an aneuploid or a polyploid may be often generated. A highly polyploid of an octoploid or higher is more likely to be hardly regenerated and it is difficult to produce a progeny of the polyploid due to the deterioration in female fertility. Therefore, it is desirable to determine the content of DNA by flow cytometry and remove a highly polyploid of an octoploid or higher.

The recombination of a mitochondrial genome by asymmetric protoplast fusion occurs randomly with high frequency. Therefore, it is desirable to produce 50 or more cytoplasmic hybrids.

(7) Acquisition of a Progeny and Selection of a High-Quality Line

The cytoplasmic hybrid thus obtained is grown and flowered, then an individual having a male sterility trait is selected, and then the individual is crosspollinated with an arbitrary *B. rapa* plant having a normal cytoplasm that serves as a pollen parent.

The cytoplasmic hybrid is often an aneuploid or a polyploid, and it is difficult to obtain a progeny thereof. Therefore, it is preferred to use a plurality of arbitrary *B. rapa* plants which are genetically varied and each of which has a normal cytoplasm as pollen parents. In order to acquire a progeny from the cytoplasmic hybrid, embryo culture is often required.

Embryo culture is a technique for excising an embryo and growing the embryo on a proper culture medium when the growth of the embryo after pollination is insufficient and the embryo may be dead if any treatment is not applied. The embryo culture can be carried out by a conventional method. In the present invention, it is desirable to excise an embryo from an ovule 7 to 10 days after crossing and culture the embryo on a half-strength MS medium supplemented with 3% of sucrose, 10% of coconut water (Sigma-Aldrich) and 0.8% of agar. A regenerated shoot is transplanted into an MS medium supplemented with 3% of sucrose and 0.8% of agar and the like to cause the rooting of the shoot, thereby regenerating a plant body. The regenerated plant body is acclimated and is then grown in a greenhouse. When the regenerated plant body flowers, an individual having male sterility is selected.

The backcrossing using an arbitrary *B. rapa* plant having a normal cytoplasm as a pollen parent and the subsequent embryo culture are continued until a progeny seed can be obtained from a male sterile individual. The individual from which a progeny seed can be obtained is subjected to recurrent backcrossing using a specific *B. rapa* plant having a normal cytoplasm as a pollen parent. With the specific *B. rapa* plant having a normal cytoplasm, it is desirable to previously select a genetically fixed line which is significantly deteriorated in growth ability when subjected to the recurrent backcrossing to an existing-cytoplasmic-male-sterile *B. rapa* plant.

When the backcrossing is carried out repeatedly using a specific *B. rapa* plant having a normal cytoplasm as a pollen parent, the nuclear genome can become the same as that of the specific *B. rapa* plant having the normal cytoplasm. As a result, the selection can be achieved by comparing a property of the cytoplasms. For the purpose of achieve satisfactory nuclear replacement, the recurrent backcrossing is desirably carried out 7 times or more. A line which has been subjected to the recurrent backcrossing is compared with the specific *B. rapa* plant having the normal cytoplasm to confirm that the line has a cytoplasmic male sterile trait and does not have any other defective trait.

EXAMPLES

The present invention will be described more specifically with reference to the following examples. However, the present invention is not limited to these examples.

Example 1: Method for Producing Ogura CMS *B. rapa* Plant Having Improved Growth Ability (1) Production of a Cytoplasm Acceptor Parent Having a High Regeneration Ability and a Normal Cytoplasm.

*B. rapa* plants generally have poor regeneration ability. Therefore, for the purpose of imparting a high regeneration ability, crossing was carried out using *B. rapa* "SH" as a seed parent and cauliflower "WC" as a pollen parent. An embryo was excised from an ovule generated 10 days after the crossing under a sterile environment, was then bedded on a MS medium having a half-strength and supplemented with 3% of sucrose, 10% of coconut water (Sigma-Aldrich) and 0.8% of agar to carry out embryo culture. After two weeks, a grown embryo plant was transplanted onto an MS medium supplemented with 3% of sucrose and 0.8% of agar. By the embryo culture, 6 individuals of an interspecific hybrid (F1) were obtained.

A petiole of each of "SH" and the interspecific hybrid individuals was cut at a length of 5 mm, was then placed on an MS medium supplemented with 1 mg/l of 2,4-D, 3% of sucrose and 0.8% of agar, and was then cultured for 3 weeks. Each of calluses grown to the size of about 1 cm was cut into a size of 1 mm, was then bedded on an MS medium supplemented with 0.3 mg/l of 4-CPPU, 0.3 mg/l of NAA, 3% of sucrose and 0.8% of agar, was then cultured for 1 month, and was then determined with respect to a regeneration ratio.

The results are shown in Table 2.

TABLE 2

Regeneration ratios of *B. rapa* interspecific hybrid plants (F1)

| Line name | Number of calluses bedded | Number of regeneration | Regeneration ratio (%) |
| --- | --- | --- | --- |
| SH | 9 | 0 | 0 |
| SH-WC1 | 9 | 5 | 56 |
| SH-WC2 | 9 | 1 | 11 |
| SH-WC3 | 9 | 3 | 33 |
| SH-WC4 | 9 | 6 | 67 |
| SH-WC5 | 9 | 1 | 11 |
| SH-WC6 | 9 | 1 | 11 |

Number of regeneration shows the number of regenerated calluses.

In Table 2, although a callus originated from "SH" was not regenerated, individuals each having a high regeneration ability were obtained in the interspecific hybrid. A line "SH-WC4" which exhibited the highest regeneration ratio was treated with colchicine to artificially diploidize the line, thereby amphidiploidizing the line. Hereinafter, amphidiploidized "SH-WC4" was referred to as "SH-WC4D". Crossing was carried out using "SH-WC4D" as a seed parent and using *B. rapa* "5" as a pollen parent. An embryo was excised from an ovule generated on day 10 after the crossing under a sterile environment, was then bedded on a half-strength MS medium supplemented with 3% of sucrose, 10% of coconut water (Sigma-Aldrich) and 0.8% of agar to carry out embryo culture. After two weeks, a grown embryo plant was transplanted onto an MS medium supplemented with 30 g/l of sucrose. By the embryo culture, 7 individuals of an interspecific hybrid (F1BC1) plant were obtained.

A petiole of each of the interspecific hybrid (F1BC1) individuals was also cut at a length of 5 mm, was then bedded on an MS medium supplemented with 1 mg/l of 2,4-D, 3% of sucrose and 0.8% of agar, and was then cultured for 3 weeks. Each of calluses grown to the size of about 1 cm was cut into a size of 1 mm, was then bedded on an MS medium supplemented with 0.3 mg/l of 4-CPPU, 0.3 mg/l of NAA, 3% of sucrose and 0.8% of agar, was then cultured for 1 month, and was then determined with respect to a regeneration ratio.

The results are shown in Table 3.

TABLE 3

Regeneration ratios of *B. rapa* interspecific hybrid plants (F1BC1)

| Line name | Number of calluses bedded | Number of regeneration | Regeneration ratio (%) |
|---|---|---|---|
| SH-WC4D-S1 | 18 | 11 | 61 |
| SH-WC4D-S2 | 18 | 8 | 44 |
| SH-WC4D-S3 | 18 | 11 | 61 |
| SH-WC4D-S4 | 18 | 6 | 33 |
| SH-WC4D-S5 | 18 | 11 | 61 |
| SH-WC4D-S6 | 18 | 0 | 0 |
| SH-WC4D-S7 | 18 | 11 | 61 |

Number of regeneration shows the number of regenerated calluses.

From the results shown in Table 3, in F1BC1, lines each having a high regeneration ratio were obtained, although the regeneration ratio varied among the lines. The lines SH-WC4D-S1, SH-WC4D-S3, SH-WC4D-S5 and SH-WC4D-S7 had the same regeneration ratio (61%) as one another, and "SH-WC4D-S5" which exhibited highest female fertility was selected as a seed parent. It was desirable to carry out the backcrossing of a *B. rapa* plant using "SH-WC4D-S5" as a seed parent. However, "SH-WC4D-S5" was produced by crossing an amphidiploid with a diploid and was therefore an allotriploid. Therefore, it was assumed that it was difficult to obtain a progeny of "SH-WC4D-S5".

Therefore, it was considered that, in order to obtain a progeny, it is needed to use *B. rapa* plants having various genotypes as pollen parents. Then, four lines "SH", "OS", "S" and "W" were prepared as pollen parents to carry out crossing. However, when hand pollination was carried out, no progeny was obtained. Therefore, "SH-WC4D-55" was placed as a seed parent in a closed-system greenhouse, each of the *B. rapa* plants of the four lines was placed beside "SH-WC4D-55", and the insect-pollinated crossing therebetween was carried out. In general, a progeny of an interspecific hybrid can be obtained more easily under a high-temperature condition. Therefore, the temperature in the greenhouse was controlled at a day temperature of 32° C. and a night temperature of 15° C. As the result of the insect-pollinated crossing, about 100 seeds were obtained, although many of the seeds were small in size. 37 seeds which had sizes close to the size of a seed of a common *B. rapa* plant were selected, and were then subjected to in vitro aseptic germination. As a result, 36 individuals of a *B. rapa* interspecific hybrid plant which was regarded as "F1BC2" were germinated. The line names of the germinated individuals were "SH-WC4D-S5-X1 to 36".

A petiole of each of the interspecific hybrid (F1BC2) individuals was cut at a length of 5 mm, was then bedded on an MS medium supplemented with 1 mg/l of 2,4-D, 3% of sucrose and 0.8% of agar, and was then cultured for 3 weeks. Each of calluses each grown to the size of about 1 cm was cut into a size of about 1 mm, was then placed on an MS medium supplemented with 0.3 mg/l of 4-CPPU, 0.3 mg/l of NAA, 3% of sucrose and 0.8% of agar, was then cultured for 1 month, and was then determined with respect to a regeneration ratio.

The results are shown in Table 4.

TABLE 4

Regeneration ratios of *B. rapa* interspecific hybrid plants (F1BC2)

| Line name | Number of calluses bedded | Number of regeneration | Regeneration ratio (%) |
|---|---|---|---|
| SH-WC4D-S5-X1 | 18 | 2 | 11 |
| SH-WC4D-S5-X2 | 18 | 0 | 0 |
| SH-WC4D-S5-X3 | 18 | 2 | 11 |
| SH-WC4D-S5-X4 | 18 | 0 | 0 |
| SH-WC4D-S5-X5 | 18 | 1 | 6 |
| SH-WC4D-S5-X6 | 18 | 3 | 17 |
| SH-WC4D-S5-X7 | 18 | 11 | 61 |
| SH-WC4D-S5-X8 | 18 | 0 | 0 |
| SH-WC4D-S5-X9 | 18 | 8 | 44 |
| SH-WC4D-S5-X10 | 18 | 0 | 0 |
| SH-WC4D-S5-X11 | 18 | 4 | 22 |
| SH-WC4D-S5-X12 | 18 | 15 | 83 |
| SH-WC4D-S5-X13 | 18 | 1 | 6 |
| SH-WC4D-S5-X14 | 18 | 9 | 50 |
| SH-WC4D-S5-X15 | 18 | 5 | 28 |
| SH-WC4D-S5-X16 | 18 | 0 | 0 |
| SH-WC4D-S5-X17 | 18 | 5 | 28 |
| SH-WC4D-S5-X18 | 18 | 1 | 6 |
| SH-WC4D-S5-X19 | 18 | 0 | 0 |
| SH-WC4D-S5-X20 | 18 | 0 | 0 |
| SH-WC4D-S5-X21 | 18 | 8 | 44 |
| SH-WC4D-S5-X22 | 18 | 7 | 39 |
| SH-WC4D-S5-X23 | 18 | 0 | 0 |
| SH-WC4D-S5-X24 | 18 | 0 | 0 |
| SH-WC4D-S5-X25 | 18 | 0 | 0 |
| SH-WC4D-S5-X26 | 18 | 13 | 72 |
| SH-WC4D-S5-X27 | 18 | 0 | 0 |
| SH-WC4D-S5-X28 | 18 | 10 | 56 |
| SH-WC4D-S5-X29 | 18 | 1 | 6 |
| SH-WC4D-S5-X30 | 18 | 0 | 0 |
| SH-WC4D-S5-X31 | 18 | 4 | 22 |
| SH-WC4D-S5-X32 | 18 | 16 | 89 |
| SH-WC4D-S5-X33 | 18 | 2 | 11 |
| SH-WC4D-S5-X34 | 18 | 0 | 0 |
| SH-WC4D-S5-X35 | 18 | 3 | 17 |
| SH-WC4D-S5-X36 | 18 | 4 | 22 |

Number of regeneration shows the number of regenerated calluses.

From the results shown in Table 4, in F1BC2, "SH-WC4D-S5-X12" had a regeneration ratio of as high as 83% and "SH-WC4D-S5-X32" had a regeneration ratio of as high as 89%, although the difference was large among the lines. "SH-WC4D-S5-X12" had poor female fertility. Therefore, "SH-WC4D-S5-X32" which had high female fertility was used as a cytoplasm acceptor parent.

(2) Preparation of a Protoplast.

(i) Isolation of Protoplasts of a *B. rapa* Interspecific Hybrid Plant Having a Normal Cytoplasm As a *B. rapa* interspecific hybrid plant having a normal cytoplasm, "SH-WC4D-S5-X32" was used. "SH-WC4D-S5-X32" was transplanted onto an MS medium supplemented with 3% of sucrose and 0.8% of agar, and was then grown for 1 month. Opened true leaves (about 1 g) were collected, were then finely cut into sizes of about 2 mm, were then immersed in a CPW salt solution (10 ml) containing 0.3% of Cellulase Y-C, 0.3% of Macerozyme R-10 and 0.5 M of mannitol, and were then allowed to leave at 25° C. for 16 hours.

The enzyme solution containing leaf tissues was filtered through a 92-μm nylon mesh to remove cell debris. A protoplast suspension thus obtained was transferred to a centrifuge tube, and was then centrifuged at 800 rpm for 5 minutes. Protoplasts produced by discarding a supernatant were suspended in a CPW salt solution (5 ml) containing 15 mM of iodoacetamide, and were then incubated at 4° C. for 15 minutes. After the incubation, the protoplast suspension which had been treated with iodoacetamide was centrifuged at 800 rpm for 5 minutes, and then a supernatant was discarded. A procedure including adding a CPW salt solution (10 ml) to the protoplast suspension, then carrying out centrifugation at 800 rpm for 5 minutes and then discarding a supernatant was repeated three times to wash the protoplasts.

The washed protoplast suspension was centrifuged at 800 rpm for 5 minutes, then a supernatant was discarded from the suspension, then a CPW salt solution (2 ml) was added to the resultant solution to suspend the protoplasts. A CPW salt solution (5 ml) supplemented with 20% of sucrose was added to a new centrifuge tube, the protoplast suspension was overlaid over the CPW salt solution, and the resultant solution was centrifuged at 800 rpm for 5 minutes. The cell debris was settled in the bottom of the centrifuge tube, the purified protoplasts floated in the CPW salt solution that was an upper layer. Then the purified protoplasts were transferred to a new centrifuge tube with a Pasteur pipette. A small portion of the suspension was removed, then the cell density of the protoplasts was determined using a hemocytometer, and then a CPW solution was added to the suspension in such a manner that the density of the protoplasts became $1 \times 10^6$ cells/ml.

(ii) Isolation of Protoplasts of Existing Ogura CMS *B. rapa* Plant

As an existing Ogura CMS *B. rapa* plant, a CMS line "HA280" which was originated from "Cabbage MS-2" in which the nucleus was replaced from *B. oleracea* to *B. rapa* by crossing was used.

Firstly, sterilized seeds were bedded on an MS medium supplemented with 3% of sucrose and 0.8% of agar, and were then grown for about 1 month at 20° C. under 16-hour lighting. Opened true leaves (about 1 g) were collected, were then finely cut into sizes of about 2 mm, were then immersed in a CPW salt solution (10 ml) containing 0.3% of Cellulase Y-C, 0.3% of Macerozyme R-10 and mannitol, and were then allowed to leave at 25° C. for 16 hours.

The enzyme solution containing leaf tissues was filtered through a 92-μm nylon mesh to remove cell debris. Protoplasts were transferred onto a plastic petri dish with a Pasteur pipette, and were then irradiated with 900 Gy of soft X-ray.

The resultant protoplast suspension was transferred into a centrifuge tube, was then centrifuged at 800 rpm for 5 minutes, then a supernatant was discarded from the suspension, and then a CPW salt solution (2 ml) was added to the resultant solution to suspend the protoplasts. A CPW salt solution (5 ml) supplemented with 20% of sucrose was added to a new centrifuge tube, the protoplast suspension was overlaid over the CPW salt solution, and the resultant solution was centrifuged at 800 rpm for 5 minutes. The cell debris was settled in the bottom of the centrifuge tube and the purified protoplasts floated in the CPW salt solution that was an upper layer. Then the purified protoplasts were transferred to a new centrifuge tube with a Pasteur pipette. A small portion of the suspension was removed, then the cell density of the protoplasts was determined using a hemocytometer, and then a CPW salt solution was added to the suspension in such a manner that the density of the protoplasts became $1 \times 10^6$ cells/ml.

(3) Fusion Treatment of the Protoplasts.

The *B. rapa* interspecific hybrid plant protoplast suspension which had been treated with iodoacetamide and the existing Ogura CMS *B. rapa* plant protoplast suspension which had been irradiated with soft X-ray were mixed together at a mixing ratio of 1:3, and the resultant mixed solution (2 ml) was dropped onto the bottom center of a 9-cm petri dish. The mixed solution was allowed to leave for 30 minutes, and then 500 g/l of a PEG solution (polyethylene glycol #6000 (nacalai tesque Inc.), 1,500 mg/l of $CaCl_2 \cdot H_2O$, 100 mg/l of $KH_2PO_4$, pH 5.5) (3 ml) was dropped around the protoplast mixed solution.

After 1 minute, a CPW salt solution (3.5 ml) was dropped around the protoplast mixed solution. After additional 2 minutes, the CPW salt solution (3.5 ml) was dropped around the protoplast mixed solution. After 5 minutes, the dropped solution was removed by gently drawing up from the edge of the petri dish and a CPW salt solution (20 ml) was added from the edge of the petri dish. The washing procedure with the CPW salt solution was repeated 3 times at 5-minute intervals.

(4) Culture of a Fused Hybrid Cell.

After the removal of the wash solution, a half-strength MS medium (10 ml) (pH 5.8) which contained 0.5 M of mannitol, 150 mg/l of casamino acid, 100 mg/l of L-glutamine, 0.03 mg/l of NAA, 0.03 mg/l of 2,4-D, 0.1 mg/l of BA and 1% of sucrose and in which the concentrate of $NH_4NO_3$ is reduced to 200 mg/l was added to the solution, and the resultant solution was cultured at 25° C. in a dark place.

Five days after the culture started, a half-strength MS medium (5 ml) (pH 5.8) which contained 150 mg/l of casamino acid, 100 mg/l of L-glutamine, 0.03 mg/l of NAA, 0.03 mg/l of 2,4-D, 0.1 mg/l of BA and 1% of sucrose and in which the concentration of $NH_4NO_3$ was reduced to 200 mg/l was added to reduce the concentration of mannitol, and then the culture was continued.

Ten days after the culture started, cells adhered onto the bottom of the petri dish were detached by rubbing with the tips of tweezers, then a solution (7.5 ml) containing 0.2 M of mannitol, 4% of sucrose and 0.6% of gellan gum was added to and mixed with the cells to form a half-solidified gel medium, and then the culture was continued.

In about 1 month after the culture started, a callus could be confirmed with naked eyes. Therefore, the callus was transplanted onto a callus growth medium (an MS medium containing 1 mg/l of 4-CPPU, 3 mg/l of NAA, 3.0% of sucrose and 0.8% of agar, pH 5.8). By carrying out 13 rounds of the fusion treatment experiment, 464 calluses were obtained.

(5) Selection of a Cytoplasmic Hybrid Having Cytoplasmic Male Sterility

As the causative gene for the cytoplasmic male sterility of Ogura CMS, orf138 occurring in a mitochondrial genome is identified by. In order to detect DNA specific to Ogura CMS by a PCR method, primers specific to orf138 gene were designed on the basis of the information on a known nucleotide sequence (Gene Bank accession No. AB055435.1) (Table 5).

TABLE 5

Primer sequences for mitochondrial genom markers used in selection of cytoplasmic hybrids

| Sequence ID (Sequence ID) | Primer name (primer name) | Primer sequence (primer seq) |
|---|---|---|
| Seq ID-1 | orf138-1F | GTCATAATCTCACTCCTACTG |
| Seq ID-2 | orf138-2R | CTCGGTCCATTTTCCACCTC |

At the stage where the callus grew to the size of 5 mm or larger, a part of the callus was sampled and then DNA was extracted therefrom. PCR was carried out using the extracted full-length genome DNA as a template and using a combination of primers orf138-1F and orf138-2R. In the PCR, denaturation at 94° C. for 1 minute, annealing at 60° C. for 2 minutes and an extension reaction at 72° C. for 2 minutes were repeated 35 cycles.

A PCR product was electrophoresed on a 1.8% agarose gel, and the gel was immersed in an ethidium bromide solution and was then photographed under irradiation with UV. Individuals each having a band corresponding to an expected size (376 bp) were selected. The 464 calluses obtained in the step (4) were examined by the PCR method with respect to the presence or absence of orf138 gene. As a result, 154 calluses had orf138 gene and were considered to be cytoplasm hybrid cells.

(6) Regeneration of a Plant Body from a Callus.

At the stage where the callus grew to the size of about 1 cm, the callus was cut into the size of about 2 mm and was then transplanted onto a regeneration medium (an MS medium containing 0.3 mg/l of 4-CPPU, 0.3 mg/l of NAA, 3.0% of sucrose and 0.8% of agar, pH 5.8).

The shoot regeneration of the callus started 2 weeks after the transplantation onto the regeneration medium. The regenerated shoot was rooted by transplanting onto an MS medium (pH 5.8) containing 3.0% of sucrose and 0.8% of agar. The 154 calluses which were confirmed to have orf138 gene were transplanted onto a regeneration medium and were then subcultured to obtain 68 lines of regenerated plant. Each of the cytoplasmic hybrids was transplanted onto a 50 cell plug tray and was then acclimated. After the acclimation, the plant was subjected to seedling raising in a glass greenhouse.

The cytoplasmic hybrids were examined with respect to polyploidy using a flow cytometer. The cytoplasmic hybrids included a diploid to an octoploid including aneuploidy.

The B. rapa interspecific hybrid plant "SH-WC4D-S5-X32" that was used as the cytoplasm acceptor parent was a diploid. The reason why the cytoplasmic hybrid had higher polyploidy was considered because a pluratiy of protoplasts originated from B. rapa interspecific hybrid plants were fused during the asymmetric protoplast fusion. The reason why the cytoplasmic hybrid had aneuploidy was considered because a part of the genome of the cytoplasm donor parent irradiated with soft X-ray was introduced. With respect to a plant having a polyploidy of octoploidy or lower, a progeny thereof may be obtained. Therefore, in this experiment, the seedling-raising of all of the individuals was continued.

Each of the cytoplasmic hybrids was seedling-raised for 1 month in a glass greenhouse, was then stored in a refrigerator set at 4° C. (lighting: 8 hours), and was then subjected to vernalization for 2 months. After the vernalization, each of the cytoplasmic hybrids was transplanted into a 15-cm pot.

Within 1 to 2 months after the vernalization, 49 lines among the 68 cytoplasmic hybrid lines reached anthesis, while 11 lines did not reach anthesis due to morphologic abnormality and 8 lines were dead due to genetic depression. Among the 49 flowered lines, 29 lines showed male sterility, while the remaining 20 lines showed male fertility. Among the male fertile 20 lines, one line lost orf138 gene, while 19 lines showed complete or partial male fertility in spite of the fact that orf138 gene was retained.

In general, in a cytoplasmic hybrid produced by asymmetric protoplast fusion, it is considered that the mitochondrial genome is recombined and the heteroplasmic state is passed down through 5 generations or more. Therefore, it is considered that orf138 gene disappeared completely in the process toward the heading of a mitochondrion from a heteroplasmic state toward a homoplasmic state. Furthermore, even when orf138 gene was introduced, there may be a case where the male sterility became unstable due to the insufficient amount thereof.

The insect-pollinated crossing was carried out in a greenhouse using the 29 lines exhibiting male sterility as seed parents and using the B. rapa plant "OS" having normal cytoplasm as a pollen parent.

As a result, a progeny seed BC1 was obtained from the 17 male sterile lines. The BC1 line was grown. In 10 lines among the 17 lines, male fertility was partially recovered, and therefore the 10 lines were disposed. Seven lines which maintained male sterility were further subjected to the insect-pollinated crossing using four B. rapa plant lines "SH", "OS", "5" and "W" each having a normal cytoplasm as pollen parents. As a result, progeny seeds BC2 were obtained from all of the 7 lines.

In the BC2 generation, seeds were obtained easily. Therefore, in BC3 or later, the B. rapa plant "SH" having a normal cytoplasm was used. It was found that "SH" showed significant deterioration in growth ability when being subjected to recurrent backcrossing to an existing Ogura CMS B. rapa plant. That is, when "SH" which is likely to be deteriorated in growth ability is used intentionally as the pollen parent for the recurrent backcrossing, the deterioration in growth ability due to the influence of a cytoplasm can be detected easily, and therefore it becomes possible to select a CMS line which is not deteriorated in growth ability.

The recurrent backcrossing was allowed to proceed using the 7 cytoplasm hybrid lines showing male sterility as seed parents and using "SH" as a pollen parent. Individuals showing a growth ability equivalent to or better than that of "SH" in each generation were selected, the recurrent backcrossing was repeated to the generation of BC7 (in the case of the recurrent backcrossing of B. rapa, until BC9) which was produced by carrying out crossing with "SH" 7 times.

The lines of each of the cytoplasm hybrids were, for example, classified into many sublines depending on the differences in properties which were believed to be caused due to heteroplasmy in the process of the recurrent backcrossing. The selection was repeated on the basis of the growth ability, the stability of male sterility, seed production properties and the shape of flowers, and finally "J1" which had best traits was selected. "J1" was offshot into several lines in each generation in the recurrent backcrossing. On the basis of the difference in growth ability, two lines "J1-3" and "J1-7" were finally selected. That is, "J1-3" and "J1-7", which were offshoot lines of "J1", were lines developed from the same fused cell, and were offshot at the BC4 generation during the process where a mitochondrion after protoplast fusion shifted toward the state of homoplasmy from the state of heteroplasmy. "J1-3" showed a growth ability superior to those of normal cytoplasm lines, and "J1-7" showed a growth ability equivalent or slightly superior to those of normal cytoplasm lines.

Seeds of BC7 of the two lines "J1-3" and "J1-7" have been internationally deposited (originally deposited) on Dec. 12, 2018 at International Patent Organism Depositary of the National Institute of Technology and Evaluation located at Room 120, 2-5-8 Kazusa Kamatari, Kisarazu-shi, Chiba-ken, Japan. The indications for identification given by the depositor and the Accession numbers of these lines are as follows:
<J1-3>
Indications for identification given by depositor: SSC-GCC-18-001 Accession No.: FERM BP-22371, and
<J1-7>
Indications for identification given by depositor: SSC-GCC-18-002 Accession No.: FERM BP-22372.

Example 2: Evaluation of Growth Ability of "J1-3" and "J1-7"

In order to confirm the usefulness of the improved CMS lines which had been developed in Example 1, a comparison test on growth ability of *B. rapa* plants each having a normal cytoplasm and a CMS cytoplasm was carried out.

As mentioned in Example 1, "SH" was found to show significant deterioration in growth ability when being subjected to recurrent backcrossing to an existing Ogura CMS *B. rapa* plant. Therefore, when the nuclear replacement is carried out by the recurrent backcrossing of the *B. rapa* plant "SH" having a normal cytoplasm to each of the cytoplasmic male sterile lines, the nuclear genome of each of the cytoplasmic male sterile lines becomes the same as that of "SH" and the deterioration in growth ability can be detected easily. Therefore, the difference in growth ability due to the difference in cytoplasms can be evaluated by growing the cytoplasmic male sterile lines under the same condition.

As a *B. rapa* plant utilizing Ogura CMS, "Violet *Brassica campestris*" which has been grown at Horti Seed Co., Ltd. in China and of which seeds have been sold in China is known. In Japan, seeds of "Ni hao fung" have been sold from Watanabe Noji Co., Ltd. Both of these plants are pak choi varieties.

In Sakata Seed Corporation, "Cabbage MS-2" which is an Ogura CMS variety which does not undergo chlorosis in a *B. oleracea* plant and a *B. rapa* plant has been developed.

These commercially available two varieties of CMS lines, one CMS line held by Sakata Seed Corporation and the improved CMS lines "J1-3" and "J1-7" developed in the present invention were subjected to the recurrent backcrossing of "SH".

In order to evaluate the growth ability of the CMS lines accurately, seeds were produced from "SH" and the above-mentioned five CMS lines under the same environment in the insect-pollinated manner.

The seeds of each of "SH" and the CMS lines were sown on a 50 cell plug tray and were grown in an artificial climate chamber which was set to a day temperature of 20° C., a night temperature of 10° C. and a lighting time of 16 hours. In order to evaluate the growth ability of young seedlings quantitatively, two weeks after the sowing, an aerial part of a young seedling of each of the lines was cut at the ground surface and the weight per head was measured. The results are shown in Table 6. In the table, the term "generation" refers to the number of frequencies of the recurrent backcrossing with "SH". For example, "BC7" means that the recurrent backcrossing was carried out 7 times using "SH" as a pollen parent.

TABLE 6

Comparison of growth ability of seedlings between existing Ogura CMS *B. rapa* plants and improved Ogura CMS *B. rapa* plants (artificial climate chamber, 2 weeks after sowing, day temperature: 20° C., night temperature: 10° C., lighting time: 16 hours)

| Line name | Distributor/ breeder | Cytoplasm | BC generation | Number of sowing | Number of germination | Germination ratio | Average weight on aerial part (g) | Relative value of weight of aerial part[1] |
|---|---|---|---|---|---|---|---|---|
| SH | SS | N | | 45 | 45 | 100% | 1.83 | 100.0 |
| CMS derived from Violet *B. campestris* | HS | S | BC10 | 15 | 14 | 93% | 1.11 | 60.7 |
| CMS derived from Ni hao fung | WN | S | BC6 | 15 | 15 | 100% | 1.39 | 76.0 |
| CMS derived from Cabbage MS-2 | SS | S | BC10 | 15 | 13 | 87% | 1.16 | 63.4 |
| J1-3 | SS | S | BC7 | 15 | 15 | 100% | 2.37 | 130.0 |
| J1-7 | SS | S | BC7 | 15 | 15 | 100% | 1.93 | 105.5 |

[1] A relative value of an average weight per head of aerial parts of each CMS line when the average weight per head of aerial parts of a *B. rapa* plant having a normal cytoplasm was defined as 100
N: Normal cytoplasm
S: Male sterile cytoplasm
SS: Sakata Seed Corporation
HS: Horti Seed Co., Ltd.
WN: Watanabe Noji Co., Ltd.

As shown in Table 6, the existing Ogura CMS lines derived from "Violet *Brassica campestris*", "Ni hao fung" and "Cabbage MS-2" had 60.7, 76.0 and 63.4, respectively, as relative values of the weights of aerial parts to that of "SH", and exhibited poor growth abilities. In contrast, the improved CMS line "J1-3" had 130.0 as a relative value of the weight of aerial parts to that of "SH", which is an extremely high growth ability. The improved CMS line "J1-7 had 105.5 as a relative value of the weight of aerial parts to that of "SH", which is equivalent to the growth ability of "SH".

Subsequently, in order to evaluate the growth ability at the stage where the plants were harvested as agricultural crops, seeds of each of "SH" and the CMS lines were sown in a 9-cm hard pot, and were then cultivated in a glass greenhouse which was adjusted to a day temperature of 25° C. and a night temperature of 15° C.

In order to evaluate the growth ability of seedlings quantitatively, 46 days after the sowing, an aerial part of a seedling of each of the lines was cut at the ground surface and the weight per head was measured. The results are shown in Table 7. In the growth ability evaluation test on young seedlings shown in Table 6, an existing Ogura CMS line derived from "Ni hao fung" was also included in the test. However, from the analysis of mitochondrial genomes in Example 3 mentioned below, the existing Ogura CMS lines derived from "Violet Brassica campestris" and "Ni hao fung" were considered to have the same cytoplasm as each other. Therefore, the growth ability test at the harvesting stage of the existing Ogura CMS line derived from "Ni hao fung" was omitted.

In contrast, with respect to the improved CMS line "J1-3", the relative value of the weight of aerial parts to that of "SH" was 130.0, and exhibited an extremely high growth ability as in the case of the test at the young seedling stage. With respect to the improved CMS line "J1-7, the relative value of the weight of aerial parts to that of "SH" was 104.4 and exhibited a growth ability equivalent to that of "SH".

As mentioned above, it was confirmed that the improved CMS lines of the present invention showed growth abilities equivalent to or higher than the B. rapa plant having a normal cytoplasm while the CMS lines derived from the existing Ogura CMS B. rapa plants showed poorer growth abilities than that of the B. rapa plant having a normal cytoplasm.

Example 3

In order to analyze the mitochondrial genomes of the improved CMS lines "J1-3" and "J1-7" developed in Example 1, comparison was made among the information on the nucleotide sequence for a known B. rapa mitochondrial genome (Gene Bank Accession No. AP017997), the information on the nucleotide sequence for a known B. oleracea mitochondrial genome (Gene Bank Accession No.

TABLE 7

Comparison of growth ability at harvesting stage between existing Ogura CMS B. rapa plants and improved Ogura CMS B. rapa plants (glass greenhouse, 46 days after sowing, day temperature: 25° C., night temperature: 18° C., natural daylength)

| Line name | Distributor/ breeder | Cytoplasm | BC generation | Number of sowing | Number of germination | Germination ratio | Average weight on aerial part (g) | Relative value of weight of aerial part[1) |
|---|---|---|---|---|---|---|---|---|
| SH | SS | N | | 30 | 29 | 97% | 15.12 | 100.0 |
| CMS derived from Violet B. campestris | HS | S | BC10 | 15 | 14 | 93% | 11.76 | 77.8 |
| CMS derived from Cabbage MS-2 | SS | S | BC10 | 15 | 12 | 80% | 12.89 | 85.3 |
| J1-3 | SS | S | BC7 | 15 | 15 | 100% | 19.65 | 130.0 |
| J1-7 | SS | S | BC7 | 15 | 15 | 100% | 15.79 | 104.4 |

[1)A relative value of an average weight per head of aerial parts of each CMS line when the average weight per head of aerial parts of a B. rapa plant having a normal cytoplasm was defined as 100.
*CMS derived from Ni hao fung was considered to have the same cytoplasm as that of Violet B. campestris, and therefore the comparative test of the CMS derived from Ni hao fung on growth ability at harvesting stage was omitted.
N: Normal cytoplasm
S: Male sterile cytoplasm
SS: Sakata Seed Corporation
HS: Horti Seed Co., Ltd.

As shown in Table 7, the CMS line derived from "Violet Brassica campestris" had 77.8 as a relative value of the weight of aerial parts to that of "SH", and the CMS line derived from "Cabbage MS-2" had 85.3, which are both confirmation of deterioration in growth ability.

In this test, the degree of deterioration in growth ability was generally smaller compared with that in the test on young seedlings. This is considered to be because there is influence of the limitation of the components of a fertilizer in an agricultural soil due to the relatively long-term pot cultivation. Comparison was made between the results shown in Table 6 and the results shown in Table 7, and there was found a correlation in the ranking of poor growth ability among the CMS lines. Consequently, with respect to the existing Ogura CMS lines derived from "Violet Brassica campestris", "Ni hao fung" and "Cabbage MS-2", it was confirmed that the growth ability was deteriorated in the background of the nuclear genome of "SH".

AP012988) and the information on the nucleotide sequence for a known R. sativus mitochondrial genome (Gene Bank Accession No. AB694744), and markers targeting 35 domains were designed on the basis of the identified SNPs (single nucleotide polymorphisms) and the information on in-del (insertion/deletion) polymorphisms (Table 8, SEQ ID NOs: 1 to 88 (seq ID-1 to ID-88)). Markers for detecting orf138 gene, which was a cytoplasmic male sterility gene originated from a R. sativus plant were designed on the basis of the information on a known nucleotide sequence (Gene Bank Accession No. AB055435.1) (Table 8, SEQ ID NO: 89, SEQ ID NO: 90 (seq ID-89, ID-90)).

Furthermore, in order to analyze chloroplast genomes, primers as shown in Table 9 were designed on the basis of the information on the nucleotide sequence for a known B. rapa chloroplast genome (Gene Bank Accession No. DQ231548) (Table 9, SEQ ID NOs: 91 to 92 (seq ID-91 to ID-92)).

TABLE 8

Primer sequences for mitochondrial genome markers

| Sequence ID | primer name | primer seq |
|---|---|---|
| Seq ID-3 | BrMt-3K-1F | ATGGCTGGTTGGGGTTAGA |
| Seq ID-4 | BrMt-3K-2R | ACGCCTATGCAATCACAGCTGAGTAATGGACTGGCGAATT |
| Seq ID-5 | BrMt-4K-1F | GCTTAGCCGAACTTCTCACCT |
| Seq ID-6 | BrMt-4K-2R | GCTGTCCACTAGCCGAAAATC |
| Seq ID-7 | BrMt-13K-2F | TTTCAGCCAGTTCTAGTCCTTTTCTTATACGCTTATTCGC |
| Seq ID-8 | BrMt-13K-3R | CCGTCGAAGGTAAGGACAGA |
| Seq ID-9 | BrMt-13K-5F | ttttttttttttttCTCTTTCTTATTGGATGGAGTCGTT |
| Seq ID-10 | BrMt-13K-10F | ttttttttttttttCTCTTTCTTATTGGATcGAGTTGTG |
| Seq ID-11 | BrMt-16K-1F | TGCATTGAGAAGGGTAGGAGA |
| Seq ID-12 | BrMt-16K-2R | AGTAGTTCAAATAGATAATCCACCTAAAATGGAACATGCG |
| Seq ID-13 | BrMt-23K-1F | TCCCCTCTGTCCCTATGTTG |
| Seq ID-14 | BrMt-23K-2R | GAGGTGTTGCCTATCCAGGT |
| Seq ID-15 | BrMt-28K-1F | GAGCATTTCTTGTTTACTCGAACAG |
| Seq ID-16 | BrMt-28K-2R | GCAATGTATCGGACTGCAAAT |
| Seq ID-17 | BrMt-36K-1F | CCTAGTCCTGAGTGCGCTGT |
| Seq ID-18 | BrMt-36K-2R | GCCCATTCCCAGTTCTTTCT |
| Seq ID-19 | BrMt-43K-1F | CTTCCTCTCTCTGTTCGGATG |
| Seq ID-20 | BrMt-43K-2R | CATGCTTTTCTTCGTCGTCA |
| Seq ID-21 | BrMt-58K-1F | GCCTCATACGGCTCCTCTAA |
| Seq ID-22 | BrMt-58K-3R | AGGATCTGGAGCGAATCCAT |
| Seq ID-23 | BrMt-63K-1F | CGCTTTGAGGTTCCCTATGA |
| Seq ID-24 | BrMt-63K-2R | ACAAGTGGGAGAGGCAGGA |
| Seq ID-25 | BrMt-65K-1F | GAGATCCAACGGTGAACAGC |
| Seq ID-26 | BrMt-65K-2R | AGGCTGCTATCCCAATAGGC |
| Seq ID-27 | BrMt-70K-1F | AGTCGAGTTATTCCGGCTTG |
| Seq ID-28 | BrMt-70K-2R | TTGTCACCACGGAGCATAAC |
| Seq ID-29 | BrMt-70K-3R | TCAGGTAAAGAAAGGCCAACA |
| Seq ID-30 | BrMt-74K-1F | GCTATGCAGTGGAAGGGAAG |
| Seq ID-31 | BrMt-74K-2R | GCAACAGGAAGAGGCAGTTG |
| Seq ID-32 | BrMt-80K-1F | TCTGGGACGAGTTGGAAGAG |
| Seq ID-33 | BrMt-80K-2R | GCGAGGATGGCTTCATAAAC |
| Seq ID-34 | BrMt-88K-1F | GGCGTGAGAGTATCCAGTCC |

TABLE 8-2

| Sequence ID | primer name | primer seq |
|---|---|---|
| Seq ID-35 | BrMt-88K-2R | GATGCAGAATTCAATGCCAAG |
| Seq ID-36 | BrMt-94K-1F | GGCATACCGAAAGGATACCA |
| Seq ID-37 | BrMt-94K-2R | ACAATGAAAGCGGCTGCCCAAGTCAGGCTCAACTCCCTAA |

TABLE 8-2-continued

| Sequence ID | primer name | primer seq |
|---|---|---|
| Seq ID-38 | BrMt-100K-1F | TAGAGCCGGTAACCCTCGTT |
| Seq ID-39 | BrMt-100K-2R | TTCAGAGCATTGTCCGAGTG |
| Seq ID-40 | BrMt-108K-1F | CCACTTGTTGGTATTCGTTGG |
| Seq ID-41 | BrMt-108K-2R | TGGCGAAAGAATCCTCGTAT |
| Seq ID-42 | BrMt-111K-1F | TTAGAGTGCAGCAGGGACAC |
| Seq ID-43 | BrMt-111K-2R | CATTCGACGTTAGAGGGACTG |
| Seq ID-44 | BrMt-111K-3F | aaaaaaaaaaaaaaaaTAGTCCCCGAAAATGCCCGTTGAT |
| Seq ID-45 | BrMt-111K-4R | AATTTCGAGTGTGATCAGAAACCT |
| Seq ID-46 | BrMt-119K-1F | CGAAAACCTTCTGTTCTGTGG |
| Seq ID-47 | BrMt-119K-2R | CGGAGCGTAACCACTTTCTT |
| Seq ID-48 | BrMt-120K-1F | TTCGTTCGTTCACTTCGTTCT |
| Seq ID-49 | BrMt-120K-2R | AGGCAGTGGATTGTGAATCCACCATGCGCGGGTTCAAGTC |
| Seq ID-50 | BrMt-120K-3R | AGGCCTTTCCTTAAGCTTCCT |
| Seq ID-51 | BrMt-133K-1F | CCAGCTGGAACTATTGACTTTACACCCTCTACCGCAGGTT |
| Seq ID-52 | BrMt-133K-5F | GATAACTCCAGTGGGCAAGAAC |
| Seq ID-53 | BrMt-133K-6R | AGTGGACTTCCTTCCTTTCCA |
| Seq ID-54 | BrMt-133K-7R | ttttttttttttttGGGAACTTTGTAATTAAGCCGAAAGA |
| Seq ID-55 | BrMt-139K-1F | ATTCCCCACCCAACCAATAC |
| Seq ID-56 | BrMt-139K-2R | AAGAGCAGCTTTCTCCGTTCT |
| Seq ID-57 | BrMt-141K-1F | GGGCTCGACAAAACAGAAAG |
| Seq ID-58 | BrMt-141K-2R | GCCCACTTCTTCACATCCAC |
| Seq ID-59 | BrMt-149K-1F | TTCAGTGTCTCAAAAGAGAATTGCTTCTATCAAGATAGGC |
| Seq ID-60 | BrMt-149K-2R | AGAAGGAGAAGGCTGAGAACG |
| Seq ID-61 | BrMt-157K-1F | CGGTTCTTTCGGGTTTGAT |
| Seq ID-62 | BrMt-157K-2R | CCAGGGATGGACGTAAACTC |
| Seq ID-63 | BrMt-161K-1F | ACTGACCCGTCTCGTATCGT |
| Seq ID-64 | BrMt-161K-2R | GACGAGTGGAATGAGGGAGA |
| Seq ID-65 | BrMt-167K-3R | TTCGTTAGTTCCGCAGCTCT |

TABLE 8-3

| Sequence ID | primer name | primer seq |
|---|---|---|
| Seq ID-66 | BrMt-167K-4F | aaaaaaaaaaaaaaaGCAGGTAGCTTGACCGCCTTACGAGT |
| Seq ID-67 | BrMt-167K-5R | AAGCCGACGTTAATAGCAGGT |
| Seq ID-68 | BrMt-167K-6F | GTGGAATTCCTACTCTCATCTCTTT |
| Seq ID-69 | BrMt-171K-1F | ATGAGTTCTCACCTTCTCTCATGGAGTAGGTAGATGAGTC |
| Seq ID-70 | BrMt-171K-2R | ttttttttttttttttACACGGGAATGAGAACAAAAGGA |
| Seq ID-71 | BrMt-171K-3F | ATGAGTTCTCACCTTCTCTCATGGAGTAGGTAGATGAGAC |
| Seq ID-72 | BrMt-175K-1F | TGAGCCTGATGAGTTGACCA |

TABLE 8-3-continued

| Sequence ID | primer name | primer seq |
|---|---|---|
| Seq ID-73 | BrMt-175K-2R | GCTCGCTTCGAAAGAAAGAAC |
| Seq ID-74 | BrMt-185K-1F | GGAAGGATCGAACCATAGGAA |
| Seq ID-75 | BrMt-185K-2R | TTGATGAGCCTTTACGAGTTGA |
| Seq ID-76 | BrMt-199K-3F | ACTTGGCCGGAAAGTGTTCT |
| Seq ID-77 | BrMt-199K-4R | ttttttttttttttGGCATTTTCGGGGACTAGCCCGGTAC |
| Seq ID-78 | BrMt-199K-5F | TAGAAAGGGAGGACAGGTTGG |
| Seq ID-79 | BrMt-199K-6R | aaaaaaaaGGAAAGAACAATGTACATGGACCAGGTGACTA |
| Seq ID-80 | BrMt-202K-1F | GTACTGACCACACCGAGGGGCAGGCCCTGAAGCGAACGAC |
| Seq ID-81 | BrMt-202K-2R | GCAGGGATACATGCATAAACAG |
| Seq ID-82 | BrMt-202K-3F | GTTCGATTCATGATCGCATCT |
| Seq ID-83 | BrMt-202K-6R | TTTCAGGCAGTGGCCGTTTAG |
| Seq ID-84 | BrMt-208K-1F | TTGCTGTATCGGAAAGTCCA |
| Seq ID-85 | BrMt-208K-2R | GCATGTCGTAAGCGAGTCAA |
| Seq ID-86 | BrMt-213K-2R | TAGGCCCATCCACCTCACTAT |
| Seq ID-87 | BrMt-213K-3F | ttttttttttCCCATGTTAACAATCTCAATGTTGCTAAAG |
| Seq ID-88 | BrMt-215K-2R | GGGTTTCCTACGACATTCCACTTGCGGAATGGAATAAAAG |
| Seq ID-89 | BrMt-215K-3F | GCAAAGCGGGAAATCCTTAC |
| Seq ID-90 | BrMt-215K-4R | aaaaaaaaaaaaaaaCGAGAGACTGGCGTTCCACGAGGAC |

TABLE 9

Primer sequences for chloroplast genome markers

| Sequence ID | primer name | primer seq |
|---|---|---|
| Seq ID-91 | BrCp-rbcL-1F | GGCAGTCAGACCAACTCTCA |
| Seq ID-92 | BrCp-rbcL-2R | ATCGGTCCACACAGTTGTCC |

As sample materials, a *B. rapa* plant having a normal cytoplasm "SH", a *B. oleracea* plant having a normal cytoplasm "G", a *R. sativus* plant having an Ogura CMS cytoplasm"KN", existing CMS lines "Violet *Brassica campestris*", "Ni hao fung" and "Cabbage MS-2", and improved CMS lines "J1-3" and "J1-7" were used.

Full-length genome DNA was extracted from each of the sample materials, and PCR was carried out using the extracted full-length genome DNA as a template and using a primer set shown in Tables 8 and 9. The conditions for the PCR include denaturation at 94° C. for 1 minute, annealing at 65° C., 60° C. or 55° C. for 1 minute, and an extension reaction at 72° C. for 2 minutes which were carried out 30 or 35 cycles (Table 10).

TABLE 10

PCR conditions for markers, and restriction enzymes

| Marker name | primer combination | PCR conditions Annealing temp. | Cycle | Restriction exzyme |
|---|---|---|---|---|
| BrMt-3K | BrMt-3K-1F & -2R | 60° C. | 30 | EcoRI, Hpy188III |
| BrMt-4K | BrMt-4K-1F & -2R | 60° C. | 30 | ApoI, HapII/MboI |
| BrMt-13K | BrMt-13K-2F & -3R | 60° C. | 30 | Bsh1236I |
|  | BrMt-13K-5F & -10F & -3R (use 3 primers) | 55° C. | 30 | MboI |
| BrMt-16K | BrMt-16K-1F & -2R | 60° C. | 30 | HhaI, XspI |
| BrMt-23K | BrMt-23K-1F & -2R | 60° C. | 30 | Hpy188I, XbaI/RsaI |
| BrMt-28K | BrMt-28K-1F & -2R | 60° C. | 30 | HpyCH4V |
| BrMt-36K | BrMt-36K-1F & -2R | 60° C. | 30 | HinfI, SpeI |
| BrMt-43K | BrMt-43K-1F & -2R | 60° C. | 30 | MluI, XspI |
| BrMt-58K | BrMt-58K-1F & -3R | 60° C. | 30 | TaqI, HpyCH4V |
| BrMt-63K | BrMt-63K-1F & -2R | 60° C. | 30 | XspI, HapII |
| BrMt-65K | BrMt-65K-1F & -2R | 60° C. | 30 | Hpy188I, Hpy188III |
| BrMt-70K | BrMt-70K-1F & -2R | 60° C. | 30 | AluI |
|  | BrMt-70K-1F & -3R | 60° C. | 30 | HinfI/Hsp92II |
| BrMt-74K | BrMt-74K-1F & -2R | 65° C. | 30 | HapII, MboII |
| BrMt-80K | BrMt-80K-1F & -2R | 60° C. | 30 | HinfI |
| BrMt-88K | BrMt-88K-1F & -2R | 60° C. | 30 | HaeIII, TaqI |
| BrMt-94K | BrMt-94K-1F & -2R | 60° C. | 30 | MseI, DdeI |
| BrMt-100K | BrMt-100K-1F & -2R | 60° C. | 30 | DraI, HaeII |
| BrMt-108K | BrMt-108K-1F & -2R | 60° C. | 30 | ApoI, DraI |
| BrMt-111K | BrMt-111K-1F & -2R | 60° C. | 30 | XspI |
|  | BrMt-111K-3F & -4R | 60° C. | 30 | MboI |

TABLE 10-continued

PCR conditions for markers, and restriction enzymes

| Marker name | primer combination | PCR conditions Annealing temp. | Cycle | Restriction exzyme |
|---|---|---|---|---|
| BrMt-119K | BrMt-119K-1F & -2R | 60° C. | 30 | Bsp119I |
| BrMt-120K | BrMt-120K-1F & -2R | 60° C. | 30 | NmuCI |
|  | BrMt-120K-1F & -3R | 60° C. | 30 | DdeI |
| BrMt-133K | BrMt-133K-1F & -6R | 60° C. | 30 | HincII |
|  | BrMt-133K-5F & -7R | 60° C. | 30 | MboI |
| BrMt-139K | BrMt-139K-1F & -2R | 60° C. | 30 | ApoI, PstI |

TABLE 10-2

| Marker name | (primer combination | PCR conditions Annealing temp. | Cycle | Restriction enzyme |
|---|---|---|---|---|
| BrMt-141K | BrMt-141K-1F & -2R | 60° C. | 30 | ClaI, HinfI |
| BrMt-149K | BrMt-149K-1F & -2R | 60° C. | 30 | HaeII |
| BrMt-157K | BrMt-157K-1F & -2R | 60° C. | 30 | Bsp119I, RsaI |
| BrMt-161K | BrMt-161K-1F & -2R | 65° C. | 30 | HapII, EcoRI |
| BrMt-167K | BrMt-167K-4F & -5R | 60° C. | 30 | HinfI |
|  | BrMt-167K-6F & -3R | 60° C. | 30 | DraI |
| BrMt-171K | BrMt-171K-1F & -2R | 60° C. | 30 | Hpy188I |
|  | BrMt-171K-3F & -2R | 60° C. | 30 | Hpy188I |
| BrMt-175K | BrMt-175K-1F & -2R | 60° C. | 30 | AflIII, ClaI |
| BrMt-185K | BrMt-185K-1F & -2R | 60° C. | 30 | HaeIII |
| BrMt-199K | BrMt-199K-3F & -4R | 60° C. | 30 | KpnI |
|  | BrMt-199K-5F & -6R | 60° C. | 30 | DdeI |
| BrMt-202K | BrMt-202K-1F & -6R | 60° C. | 35 | Hpy99I |
|  | BrMt-202K-3F & -2R | 60° C. | 30 | HinfI |
| BrMt-208K | BrMt-208K-1F & -2R | 60° C. | 30 | StyI, SadI |
| BrMt-213K | BrMt-213K-3F & -2R | 60° C. | 30 | AluI, Alw26I |
| BrMt-215K | BrMt-215K-3F & -2R | 60° C. | 30 | AluI |
|  | BrMt-215K-3F & -4R | 60° C. | 30 | AvaII |
| orf138 | orf138-1F $ -2R | 60° C. | 30 | (dominant type marker) |
| BrCp-rbcL | BrCp-rbcL-1F & -2R | 60° C. | 30 | TaqI, HapII |

In order to carry out the PCR-RFLP analysis for detecting polymorphisms among a *B. rapa* plant, a *B. oleracea* plant and an *R. sativus* plant, each of the PCR products was treated with a restriction enzyme shown in Table 10. Each of the PCR products was electrophoresed on a 1.8% agarose gel, and the gel was immersed in an ethidium bromide solution and was then photographed under irradiation with UV to examine about polymorphisms.

The results of the analysis of mitochondrial genomes employing the PCR-RFLP method are shown in Table 11, and the results of the analysis of chloroplast genomes are shown in Table 12. In Tables 11 and 12, "Br" means "a *B. rapa* type", "Bo" means "a *B. oleracea* type, and "Rs" means "a *R. sativus* type". "0" means the fact that the detection with the marker was not observed, and "1" means the fact that the detection with the marker was observed. The results of the analysis of mitochondrial genomes are shown in Table 13. In Table 13, a numeral value shown in ( ) is a percentage of each mitochondrial genome type relative to the total number of markers used. The total number of the markers used is 35, i.e., markers Nos. 1 to 35 in Table 11, which were used in the analysis of mitochondrial genomes, in which orf138 shown in Table 11 was excluded.

TABLE 11

Results of analysis of mitochondrial genomes of lines

| No. | Marker name | Target domain in mitochondrial genome of *B. rapa* (AP017997) | 1 | 2 | 3 | 4 | 5 | 6 | 7 | 8 |
|---|---|---|---|---|---|---|---|---|---|---|
| 1 | BrMt-3K | 2971-3176 | Br | Bo | Rs | Br | Br | Bo | Bo | Bo |
| 2 | BrMt-4K | 4011-4485 | Br | Bo | Rs | Br | Br | Bo | Bo | Bo |
| 3 | BrMt-13K | 13842-14054 | Br | Bo | Rs | Rs | Rs | Bo | Br | Br |
| 4 | BrMt-16K | 16688-16920 | Br | Bo | Rs | Br | Br | Bo | Br | Br |
| 5 | BrMt-23K | 23503-24919 | Br | Bo | Rs | Rs | Rs | Bo | Br | Br |
| 6 | BrMt-28K | 28110-28345 | Br | Bo | Rs | Br | Br | Bo | Br | Br |
| 7 | BrMt-36K | 36077-38274 | Br | Bo | Rs | Br | Br | Bo | Bo | Bo |
| 8 | BrMt-43K | 43545-44895 | Br | Bo | Rs | Br | Br | Bo | Br | Br |
| 9 | BrMt-58K | 58114-58512 | Br | Bo | Rs | Br | Br | Bo | Br | Br |
| 10 | BrMt-63K | 63101-64250 | Br | Bo | Rs | Br | Br | Bo | Br | Br |
| 11 | BrMt-65K | 65457-66680 | Br | Bo | Rs | Br | Br | Bo | Bo | Bo |
| 12 | BrMt-70K | 69956-70743 | Br | Bo | Rs | Br | Br | Bo | Br | Br |
| 13 | BrMt-74K | 74153-74714 | Br | Bo | Rs | Rs | Rs | Bo | Br | Br |
| 14 | BrMt-80K | 80890-81594 | Br | Bo | Rs | Br | Br | Bo | Bo | Bo |
| 15 | BrMt-88K | 87960-89338 | Br | Bo | Rs | Br | Br | Bo | Br | Br |
| 16 | BrMt-94K | 94463-95504 | Br | Bo | Rs | Br | Br | Bo | Bo | Bo |
| 17 | BrMt-100K | 100277-101808 | Br | Bo | Rs | Br | Br | Rs | Br | Br |
| 18 | BrMt-108K | 108026-108755 | Br | Bo | Rs | Br | Br | Rs | Rs | Rs |
| 19 | BrMt-111K | 110830-112749 | Br | Bo | Rs | Br | Br | Rs | Br | Br |
| 20 | BrMt-119K | 118848-119345 | Br | Bo | Rs | Rs | Rs | Bo | Bo | Bo |
| 21 | BrMt-120K | 120098-120907 | Br | Bo | Rs | Rs | Rs | Rs | Br | Br |
| 22 | BrMt-133K | 132949-133973 | Br | Bo | Rs | Rs | Rs | Bo | Bo | Bo |
| 23 | BrMt-139K | 138957-139729 | Br | Bo | Rs | Rs | Rs | Bo | Bo | Bo |
| 24 | BrMt-141K | 140920-141483 | Br | Bo | Rs | Br | Br | Bo | Br | Br |
| 25 | BrMt-149K | 149290-149784 | Br | Bo | Rs | Rs | Rs | Bo | Br | Br |
| 26 | BrMt-157K | 157126-157579 | Br | Bo | Rs | Br | Br | Bo | Br | Br |
| 27 | BrMt-161K | 161123-161841 | Br | Bo | Rs | Br | Br | Bo | Br | Br |
| 28 | BrMt-167K | 168083-169498 | Br | Bo | Rs | Rs | Rs | Rs | Rs | Rs |

TABLE 11-2

| No. | Marker name | Target domain in mitochondrial genome of *B. rapa* (AP017997) | 1 | 2 | 3 | 4 | 5 | 6 | 7 | 8 |
|---|---|---|---|---|---|---|---|---|---|---|
| 29 | BrMt-171K | 171418-171566 | Br | Bo | Rs | Rs | Rs | Bo | Bo | Bo |
| 30 | BrMt-185K | 185202-185874 | Br | Bo | Rs | Rs | Rs | Bo | Br | Br |
| 31 | BrMt-199K | 199292-199819 | Br | Bo | Rs | Br | Br | Rs | Br | Br |
| 32 | BrMt-202K | 202541-203276 | Br | Bo | Rs | Rs | Rs | Rs | Rs | Rs |
| 33 | BrMt-208K | 208529-209095 | Br | Bo | Rs | Rs | Rs | Bo | Bo | Bo |
| 34 | BrMt-213K | 212470-213205 | Br | Bo | Rs | Br | Br | Bo | Br | Br |
| 35 | BrMt-215K | 215630-215886 | Br | Bo | Rs | Br | Br | Bo | Br | Br |
| | orf138 | (not in *B. rapa*) | 0 | 0 | 1 | 1 | 1 | 1 | 1 | 1 |

(Description of Symbols and Values in Tables)

1: *B. rapa* (normal cytoplasm)

2: *B. oleracea* (normal cytoplasm)

4: CMS derived from Violet *B. campestris*

5: CMS derived from Ni hao fung

6: CMS derived from Cabbage MS-2

Br: *B. rapa* type

Bo: *B. oleracea* type

Rs: *R. sativus* type

0: not detected with marker

1: detected with marker

12: Results of analysis of chloroplast genomes of CMS lines

| Marker name | CMS derived from Violet B. campestris | CMS derived from Ni hao fung | CMS derived from Cabbage MS-2 | J1-3 | J1-7 |
|---|---|---|---|---|---|
| BrCp-rbcL | Br | Br | Bo | Br | Br |

TABLE 13

Summary of results of analysis of mitochondrial genomes of CMS lines

| Type of mitochondrial genome | Number of markers identified as each type of mitochondrial genome ||||| 
|---|---|---|---|---|---|
| | CMS derived from Violet B. campestris | CMS derived from Ni hao fung | CMS derived from Cabbage MS-2 | J1-3 | J1-7 |
| B. rapa type | 22(63%) | 22(63%) | 0(0%) | 21(60%) | 21(60%) |
| B. oleracea type | 0(0%) | 0(0%) | 27(77%) | 11(31%) | 11(31%) |
| R. sativus type | 13(37%) | 13(37%) | 8(23%) | 3(9%) | 3(9%) |

A numeral value shown in ( ) is a percentage of each mitochondrial genome type relative to the total number of markers used. The total number of the markers used is 35, i.e., markers Nos. 1 to 35, which were used in the analysis of mitochondrial genomes, in which orf138 shown in Table 11 was excluded.

Each of the CMS lines derived from "Violet Brassica campestris" and "Ni hao fung" had a chloroplast originated from B. rapa and had a recombinant mitochondrial genome between B. rapa and R. sativus. The pattern of the recombination was identical among the 35 markers. Therefore, the CMS cytoplasms were considered to be originated from the same origin. Furthermore, because each of the CMS lines had orf138 gene and a chloroplast originated from B. rapa and had a recombinant mitochondrial genome between B. rapa and R. sativus, it was considered that these CMS lines were developed by the asymmetric protoplast fusion between a R. sativus plant having an Ogura CMS cytoplasm and a B. rapa plant having a normal cytoplasm. With respect to this cytoplasmic constitution, no report other than "new OguCMS" which has been disclosed in Patent Literature 2 is known. Therefore, it is considered that the cytoplasms of "Violet Brassica campestris" and "Ni hao fung" were highly probably developed by the method disclosed in Patent Literature 2.

In the results shown in Table 13, each of the recombinant mitochondrial genomes in the CMS line derived from "Violet Brassica campestris" and the CMS line derived from "Ni hao fung" had 63% of B. rapa-type mitochondrial DNA and 37% of R. sativus-type mitochondrial DNA. The reason for the deterioration in growth ability shown in Tables 6 and 7 was considered to be because many R. sativus-type mitochondrial genomes were introduced together with orf138 into a B. rapa plant and, as a result, the incompatibility between the nuclear genome of the B. rapa plant and the mitochondrial genome originated from the R. sativus plant occurred.

"Cabbage MS-2" had 77% of B. oleracea-type mitochondrial DNA and 23% of R. sativus-type mitochondrial DNA, in which the chloroplast was originated from B. oleracea. The reason for the deterioration in growth ability shown in Tables 6 and 7 was considered to be because the chloroplast was originated from B. oleracea and the presence of mitochondrial genomes originated from B. oleracea and R. sativus induced the incompatibility with the nuclear genome of the B. rapa plant, which resulted in the deterioration in growth ability. However, the level of the deterioration in growth ability was intermediate between "Violet Brassica campestris" and "Ni hao fung" and obvious growth abnormality such as chlorosis was not induced. Therefore, it was assumed that there was not a significant difference in the influence on the growth ability of a B. rapa plant between a mitochondrial genome of a B. oleracea type and a mitochondrial genome of a B. rapa type. The Mitochondrial genome of each of "J1-3" and "J1-7" which were developed according to the present invention had 60% of a B. rapa-type mitochondrial DNA and 31% of a B. oleracea-type mitochondrial DNA, in which the percentage of R. sativus-type mitochondrial DNA was only 9%.

From the above-mentioned results, it was considered that, in the method of the present invention, the efficiency of production of a cytoplasmic hybrid of a B. rapa plant by asymmetric protoplast fusion was increased and, as a result, it became possible to select a CMS line in which the introduction of an R. sativus mitochondrial genome, which is the cause for the deterioration of growth ability, was minimized while introducing the cytoplasmic male sterility gene orf138. As a result, the obtained CMS line was improved in the compatibility between the B. rapa plant and the mitochondrial genome while retaining cytoplasmic male sterility, leading to the improvement in growth ability.

As mentioned above, the reason for the improvement in growth ability in "J1-3" and "J1-7" is not elucidated yet. In the development of CMS plants, however, it is sufficient to obtain a practically useful single line of a CMS plant, because an arbitrary B. rapa plant can be provided with CMS freely by carrying out the recurrent backcrossing using the CMS plant as a seed parent and using an arbitrary B. rapa plant as a pollen parent to achieve nuclear replacement, which is practically acceptable. That is, when the Ogura CMS B. rapa plant having an improved growth ability, which has been deposited in the invention of the present application, is used, it becomes possible to provide an arbitrary B. rapa plant with CMS freely.

The results shown in Table 11 are one example of the results of the analysis of individuals exhibiting cytoplasmic male sterility, and an Ogura CMS B. rapa plant having an improved growth ability does not always show these band patterns.

Example 4

The productivity of seeds of a CMS line directly correlates with the productivity of a parent seed and a commercial seed. Therefore, comparison of seed productivity was made among CMS lines. As sample materials, a B. rapa plant having a normal cytoplasm "SH", existing CMS lines "Violet Brassica campestris", "Ni hao fung" and "Cabbage MS-2", and improved CMS lines "J1-3" and "J1-7" were used.

Ten seeds of each of the lines were sown onto a 50 cell plug tray and were then raised into seedlings in a glass greenhouse having a day temperature of 23° C. and a night temperature of 15° C. for 1 month, and were then stored in a refrigerator set at 4° C. (lighting time: 8 hours) for 2 months to achieve vernalization. After the vernalization was completed, two plants of each of the lines were planted into No. 10 plant pots and were then cultivated in a glass greenhouse at a day temperature of 23° C. and a night temperature of 15° C. The crosspollination was carried out in an insect-pollinated manner. After fruits were born, seeds were carefully harvested, and the amount of seeds harvested per plant was examined.

In Table 14, the results of the average seed harvest amount per plant in the lines are shown.

TABLE 14

Comparison of seed harvest amount among lines

| No. | Name of line | Distributor/ breeder | Cyto- plasm | Average seed harvest amount per plant (g) | Relative value of seed harvest amount[1] |
|---|---|---|---|---|---|
| 1 | SH | SS | N | 8.29 | 100.0 |
| 2 | Violet B. campestris | HS | S | 5.80 | 70.0 |
| 3 | Ni hao fung | WN | S | 5.49 | 66.2 |
| 4 | Cabbage MS-2 | SS | S | 1.60 | 19.3 |
| 5 | J1-3 | SS | S | 12.37 | 149.1 |
| 6 | J1-7 | SS | S | 12.16 | 146.6 |

[1]A relative value of an average seed harvest amount in each CMS line when the average seed harvest amount per plant in a B. rapa having a normal cytoplasm "SH" was defined as 100.

When the seed harvest amount of the *B. rapa* plant having a normal cytoplasm "SH" was 100, the relative value of the seed harvest amount of each of the CMS lines respectively derived from "Violet *Brassica campestris*" and "Ni hao fung" was about 70. These CMS lines were deteriorated in growth ability and the plants thereof were therefore smaller in size compared with "SH". This deteriorated growth ability seemed to affect the decrease in seed harvest amount. The relative value of seed harvest amount of "Cabbage MS-2" was 19.3, which was extremely poor. Before the vernalization, the growth of the CMS line derived from "Cabbage MS-2" was equivalent to those of the CMS lines derived from "Violet *Brassica campestris*" and "Ni hao fung". However, after the vernalization, the growth was extremely deteriorated temporally. This was considered to be because this line was likely to be damaged by a low temperature. With respect to "J1-3" and "J1-7" which were improved CMS lines, the sizes of plants were equivalent to or larger than that of "SH" over an entire period. As a result, the relative values of seed harvest amounts became respectively 149.2 and 146.7, and it was confirmed that these lines had high seed productivity and had no problem with respect to female fertility.

The invention claimed is:

1. A cytoplasmic male sterile *Brassica rapa* plant having a growth ability equivalent to that of a *Brassica rapa* plant having normal cytoplasm wherein the plant contains a mitochondrial genome originated from a plant identified by Accession No. FERM BP-22371 or Accession No. FERM BP-22372.

2. The cytoplasmic male sterile *Brassica rapa* plant according to claim 1, wherein the cytoplasmic male sterile *Brassica rapa* plant has, in the mitochondrial genome thereof, DNA molecules respectively originating from a mitochondrial genome of a *Raphanus sativus* plant, a mitochondrial genome of a *Brassica oleracea* plant and a mitochondrial genome of a *Brassica rapa* plant.

3. The cytoplasmic male sterile *Brassica rapa* plant according to claim 1, wherein the cytoplasmic male sterile *Brassica rapa* plant is produced by carrying out asymmetric protoplast fusion using a *Brassica rapa* interspecific hybrid plant having a normal cytoplasm as a cytoplasm acceptor parent.

4. The cytoplasmic male sterile *Brassica rapa* plant according to claim 1, wherein the cytoplasmic male sterile *Brassica rapa* plant is produced by carrying out asymmetric protoplast fusion using a cytoplasmic male sterile *Brassica plant* having a cytoplasmic male sterility gene originated from a *Raphanus sativus* plant as a cytoplasm donor parent.

5. The cytoplasmic male sterile *Brassica rapa* plant thereof according to claim 1, wherein the cytoplasmic male sterile *Brassica rapa* plant is produced by carrying out asymmetric protoplast fusion using a cytoplasmic male sterile *Brassica plant* originated from a cytoplasmic male sterile *Brassica oleracea* plant as a cytoplasm donor parent.

6. The cytoplasmic male sterile *Brassica rapa* plant according to claim 1, wherein the cytoplasmic male sterile *Brassica rapa* plant is produced by carrying out asymmetric protoplast fusion using a cytoplasmic male sterile *Brassica rapa* plant originated from a cytoplasmic male sterile *Brassica oleracea* plant as a cytoplasm donor parent.

7. The cytoplasmic male sterile *Brassica rapa* plant according to claim 1, wherein the cytoplasmic male sterile *Brassica rapa* plant is produced by carrying out asymmetric protoplast fusion using an existing-cytoplasmic-male-sterile *Brassica* plant as a cytoplasm donor parent and using a *Brassica rapa* interspecific hybrid plant having a normal cytoplasm as a cytoplasm acceptor parent.

8. The cytoplasmic male sterile *Brassica rapa* plant according to claim 3, wherein the interspecific hybrid plant is originated from a *Brassica oleracea* plant and a *Brassica rapa* plant.

9. The cytoplasmic male sterile *Brassica rapa* plant according to claim 7, wherein the existing-cytoplasmic-male-sterile *Brassica* plant is an existing-cytoplasmic-male-sterile *Brassica rapa* plant.

10. The cytoplasmic male sterile *Brassica rapa* plant according to claim 7, wherein the existing-cytoplasmic-male-sterile *Brassica plant* is originated from a cytoplasmic male sterile *Brassica oleracea* plant.

11. The cytoplasmic male sterile *Brassica rapa* plant according to claim 4, wherein the cytoplasm donor parent has a cytoplasmic male sterility gene orf138.

12. A cytoplasmic male sterile *Brassica rapa* plant according to claim 2,
wherein, the cytoplasmic male sterile *Brassica rapa* plant or the progeny thereof is able to be produced by carrying out asymmetric protoplast fusion using a *Brassica rapa* interspecific hybrid plant having a normal cytoplasm as a cytoplasm acceptor parent.

13. The cytoplasmic male sterile *Brassica rapa* plant according to claim 1, wherein at least one of mitochondrial DNA molecules respectively identified by mitochondrial genome markers BrMt-13K, BrMt-23K, BrMt-74K, BrMt-120K, BrMt-149K and BrMt-185K is of a *Brassica rapa* type.

14. The cytoplasmic male sterile *Brassica rapa* plant according to claim 1, wherein at least one of mitochondrial DNA molecules which is respectively identified by mitochondrial genome markers BrMt-119K, BrMt-133K, BrMt-139K, BrMt-171K and BrMt-208K is of a *Brassica oleracea* type.

15. The cytoplasmic male sterile *Brassica rapa* plant according to claim 1, wherein each of mitochondrial DNA molecules which is respectively identified by mitochondrial genome markers BrMt-13K, BrMt-16K, BrMt-23K, BrMt-28K, BrMt-43K, BrMt-58K, BrMt-63K, BrMt-70K, BrMt-74K, BrMt-88K, BrMt-100K, BrMt-111K, BrMt-120K, BrMt-141K, BrMt-149K, BrMt-157K, BrMt-161K, BrMt-185K, BrMt-199K, BrMt-213K and BrMt-215K is of a *Brassica rapa* type and each of mitochondrial DNA which is respectively identified by mitochondrial genome markers BrMt-3K, BrMt-4K, BrMt-36K, BrMt-65K, BrMt-80K, BrMt-94K, BrMt-119K, BrMt-133K, BrMt-139K, BrMt-171K and BrMt-208K is of a *Brassica oleracea* type.

16. A cytoplasmic male sterile *Brassica rapa* plant according to claim 1, which is identified by Accession No. FERM BP-22371 or Accession No. FERM BP-22372.

17. The cytoplasmic male sterile *Brassica rapa* plant according to claim 1, wherein the cytoplasmic male sterile *Brassica rapa* plant is produced by carrying out asymmetric protoplast fusion using a cytoplasmic male sterile *Brassica rapa* plant having a mitochondrial genome of a plant identified by Accession No. FERM BP-22371 or Accession No. FERM BP-22372 as a cytoplasm donor parent and a *Brassica rapa* interspecific hybrid plant having a normal cytoplasm is used as a cytoplasm acceptor parent.

18. A part of a plant body of a cytoplasmic male sterile *Brassica rapa* plant as recited in claim 1.

19. A seed of a cytoplasmic male sterile *Brassica rapa* plant as recited on claim 1.

20. A method for producing a first filial generation seed, comprising the steps of: crossing as a seed parent a cytoplasmic male sterile *Brassica rapa* plant as recited in claim 1 and as a pollen parent a *Brassica rapa* plant capable of being crossed with said plant and collecting a first filial generation seed from the seed parent after the crossing.

21. A method for producing a *Brassica rapa* plant exhibiting cytoplasmic male sterility,
the method comprising carrying out the recurrent backcrossing of an arbitrary *Brassica rapa* plant to a cytoplasmic male sterile *Brassica rapa* plant as recited in claim 1 to achieve cytoplasmic replacement.

* * * * *

SEQUENCE LISTING

<160> NUMBER OF SEQ ID NOS: 92

<210> SEQ ID NO 1
<211> LENGTH: 21
<212> TYPE: DNA
<213> ORGANISM: Artificial Sequence
<220> FEATURE:
<223> OTHER INFORMATION: primer

<400> SEQUENCE: 1
gtcataatct cactcctact g                                   21

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
ctcggtccat tttccacctc                                     20

<210> SEQ ID NO 3
<211> LENGTH: 19
<212> TYPE: DNA
<213> ORGANISM: Artificial Sequence
<220> FEATURE:
<223> OTHER INFORMATION: primer

<400> SEQUENCE: 3
atggctggtt ggggttaga                                      19

<210> SEQ ID NO 4
<211> LENGTH: 40
<212> TYPE: DNA
<213> ORGANISM: Artificial Sequence
<220> FEATURE:
<223> OTHER INFORMATION: primer

<400> SEQUENCE: 4
acgcctatgc aatcacagct gagtaatgga ctggcgaatt          40

<210> SEQ ID NO 5
<211> LENGTH: 21
<212> TYPE: DNA
<213> ORGANISM: Artificial Sequence
<220> FEATURE:
<223> OTHER INFORMATION: primer

<400> SEQUENCE: 5
gcttagccga acttctcacc t          21

<210> SEQ ID NO 6
<211> LENGTH: 21
<212> TYPE: DNA
<213> ORGANISM: Artificial Sequence
<220> FEATURE:
<223> OTHER INFORMATION: primer

<400> SEQUENCE: 6
gctgtccact agccgaaaat c          21

<210> SEQ ID NO 7
<211> LENGTH: 40
<212> TYPE: DNA
<213> ORGANISM: Artificial Sequence
<220> FEATURE:
<223> OTHER INFORMATION: primer

<400> SEQUENCE: 7
tttcagccag ttctagtcct tttcttatac gcttattcgc          40

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
ccgtcgaagg taaggacaga          20

<210> SEQ ID NO 9
<211> LENGTH: 40
<212> TYPE: DNA
<213> ORGANISM: Artificial Sequence
<220> FEATURE:
<223> OTHER INFORMATION: primer

<400> SEQUENCE: 9
tttttttttt ttttctctt tcttattgga tggagtcgtt          40

<210> SEQ ID NO 10
<211> LENGTH: 40
<212> TYPE: DNA
<213> ORGANISM: Artificial Sequence
<220> FEATURE:
<223> OTHER INFORMATION: primer

<400> SEQUENCE: 10
tttttttttt ttttctctt tcttattgga tcgagttgtg          40

<210> SEQ ID NO 11
<211> LENGTH: 21
<212> TYPE: DNA

```
<213> ORGANISM: Artificial Sequence
<220> FEATURE:
<223> OTHER INFORMATION: primer

<400> SEQUENCE: 11
tgcattgaga agggtaggag a                                              21

<210> SEQ ID NO 12
<211> LENGTH: 40
<212> TYPE: DNA
<213> ORGANISM: Artificial Sequence
<220> FEATURE:
<223> OTHER INFORMATION: primer

<400> SEQUENCE: 12
agtagttcaa atagataatc cacctaaaat ggaacatgcg                          40

<210> SEQ ID NO 13
<211> LENGTH: 20
<212> TYPE: DNA
<213> ORGANISM: Artificial Sequence
<220> FEATURE:
<223> OTHER INFORMATION: primer

<400> SEQUENCE: 13
tcccctctgt ccctatgttg                                                20

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
gaggtgttgc ctatccaggt                                                20

<210> SEQ ID NO 15
<211> LENGTH: 25
<212> TYPE: DNA
<213> ORGANISM: Artificial Sequence
<220> FEATURE:
<223> OTHER INFORMATION: primer

<400> SEQUENCE: 15
gagcatttct tgtttactcg aacag                                          25

<210> SEQ ID NO 16
<211> LENGTH: 21
<212> TYPE: DNA
<213> ORGANISM: Artificial Sequence
<220> FEATURE:
<223> OTHER INFORMATION: primer

<400> SEQUENCE: 16
gcaatgtatc ggactgcaaa t                                              21

<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17
cctagtcctg agtgcgctgt                                                20
```

```
<210> SEQ ID NO 18
<211> LENGTH: 20
<212> TYPE: DNA
<213> ORGANISM: Artificial Sequence
<220> FEATURE:
<223> OTHER INFORMATION: primer

<400> SEQUENCE: 18
gcccattccc agttctttct                                                    20

<210> SEQ ID NO 19
<211> LENGTH: 21
<212> TYPE: DNA
<213> ORGANISM: Artificial Sequence
<220> FEATURE:
<223> OTHER INFORMATION: primer

<400> SEQUENCE: 19
cttcctctct ctgttcggat g                                                  21

<210> SEQ ID NO 20
<211> LENGTH: 20
<212> TYPE: DNA
<213> ORGANISM: Artificial Sequence
<220> FEATURE:
<223> OTHER INFORMATION: primer

<400> SEQUENCE: 20
catgcttttc ttcgtcgtca                                                    20

<210> SEQ ID NO 21
<211> LENGTH: 20
<212> TYPE: DNA
<213> ORGANISM: Artificial Sequence
<220> FEATURE:
<223> OTHER INFORMATION: primer

<400> SEQUENCE: 21
gcctcatacg gctcctctaa                                                    20

<210> SEQ ID NO 22
<211> LENGTH: 20
<212> TYPE: DNA
<213> ORGANISM: Artificial Sequence
<220> FEATURE:
<223> OTHER INFORMATION: primer

<400> SEQUENCE: 22
aggatctgga gcgaatccat                                                    20

<210> SEQ ID NO 23
<211> LENGTH: 20
<212> TYPE: DNA
<213> ORGANISM: Artificial Sequence
<220> FEATURE:
<223> OTHER INFORMATION: primer

<400> SEQUENCE: 23
cgctttgagg ttccctatga                                                    20

<210> SEQ ID NO 24
<211> LENGTH: 19
<212> TYPE: DNA
<213> ORGANISM: Artificial Sequence
<220> FEATURE:
```

```
<223> OTHER INFORMATION: primer

<400> SEQUENCE: 24
acaagtggga gaggcagga                                                    19

<210> SEQ ID NO 25
<211> LENGTH: 20
<212> TYPE: DNA
<213> ORGANISM: Artificial Sequence
<220> FEATURE:
<223> OTHER INFORMATION: primer

<400> SEQUENCE: 25
gagatccaac ggtgaacagc                                                   20

<210> SEQ ID NO 26
<211> LENGTH: 20
<212> TYPE: DNA
<213> ORGANISM: Artificial Sequence
<220> FEATURE:
<223> OTHER INFORMATION: primer

<400> SEQUENCE: 26
aggctgctat cccaataggc                                                   20

<210> SEQ ID NO 27
<211> LENGTH: 20
<212> TYPE: DNA
<213> ORGANISM: Artificial Sequence
<220> FEATURE:
<223> OTHER INFORMATION: primer

<400> SEQUENCE: 27
agtcgagtta ttccggcttg                                                   20

<210> SEQ ID NO 28
<211> LENGTH: 20
<212> TYPE: DNA
<213> ORGANISM: Artificial Sequence
<220> FEATURE:
<223> OTHER INFORMATION: primer

<400> SEQUENCE: 28
ttgtcaccac ggagcataac                                                   20

<210> SEQ ID NO 29
<211> LENGTH: 21
<212> TYPE: DNA
<213> ORGANISM: Artificial Sequence
<220> FEATURE:
<223> OTHER INFORMATION: primer

<400> SEQUENCE: 29
tcaggtaaag aaaggccaac a                                                 21

<210> SEQ ID NO 30
<211> LENGTH: 20
<212> TYPE: DNA
<213> ORGANISM: Artificial Sequence
<220> FEATURE:
<223> OTHER INFORMATION: primer

<400> SEQUENCE: 30
gctatgcagt ggaagggaag                                                   20
```

```
<210> SEQ ID NO 31
<211> LENGTH: 20
<212> TYPE: DNA
<213> ORGANISM: Artificial Sequence
<220> FEATURE:
<223> OTHER INFORMATION: primer

<400> SEQUENCE: 31
gcaacaggaa gaggcagttg                                              20

<210> SEQ ID NO 32
<211> LENGTH: 20
<212> TYPE: DNA
<213> ORGANISM: Artificial Sequence
<220> FEATURE:
<223> OTHER INFORMATION: primer

<400> SEQUENCE: 32
tctgggacga gttggaagag                                              20

<210> SEQ ID NO 33
<211> LENGTH: 20
<212> TYPE: DNA
<213> ORGANISM: Artificial Sequence
<220> FEATURE:
<223> OTHER INFORMATION: primer

<400> SEQUENCE: 33
gcgaggatgg cttcataaac                                              20

<210> SEQ ID NO 34
<211> LENGTH: 20
<212> TYPE: DNA
<213> ORGANISM: Artificial Sequence
<220> FEATURE:
<223> OTHER INFORMATION: primer

<400> SEQUENCE: 34
ggcgtgagag tatccagtcc                                              20

<210> SEQ ID NO 35
<211> LENGTH: 21
<212> TYPE: DNA
<213> ORGANISM: Artificial Sequence
<220> FEATURE:
<223> OTHER INFORMATION: primer

<400> SEQUENCE: 35
gatgcagaat tcaatgccaa g                                            21

<210> SEQ ID NO 36
<211> LENGTH: 20
<212> TYPE: DNA
<213> ORGANISM: Artificial Sequence
<220> FEATURE:
<223> OTHER INFORMATION: primer

<400> SEQUENCE: 36
ggcataccga aaggatacca                                              20

<210> SEQ ID NO 37
<211> LENGTH: 40
<212> TYPE: DNA
<213> ORGANISM: Artificial Sequence
<220> FEATURE:
<223> OTHER INFORMATION: primer
```

<400> SEQUENCE: 37
acaatgaaag cggctgccca agtcaggctc aactccctaa                                40

<210> SEQ ID NO 38
<211> LENGTH: 20
<212> TYPE: DNA
<213> ORGANISM: Artificial Sequence
<220> FEATURE:
<223> OTHER INFORMATION: primer

<400> SEQUENCE: 38
tagagccggt aaccctcgtt                                                      20

<210> SEQ ID NO 39
<211> LENGTH: 20
<212> TYPE: DNA
<213> ORGANISM: Artificial Sequence
<220> FEATURE:
<223> OTHER INFORMATION: primer

<400> SEQUENCE: 39
ttcagagcat tgtccgagtg                                                      20

<210> SEQ ID NO 40
<211> LENGTH: 21
<212> TYPE: DNA
<213> ORGANISM: Artificial Sequence
<220> FEATURE:
<223> OTHER INFORMATION: primer

<400> SEQUENCE: 40
ccacttgttg gtattcgttg g                                                    21

<210> SEQ ID NO 41
<211> LENGTH: 20
<212> TYPE: DNA
<213> ORGANISM: Artificial Sequence
<220> FEATURE:
<223> OTHER INFORMATION: primer

<400> SEQUENCE: 41
tggcgaaaga atcctcgtat                                                      20

<210> SEQ ID NO 42
<211> LENGTH: 20
<212> TYPE: DNA
<213> ORGANISM: Artificial Sequence
<220> FEATURE:
<223> OTHER INFORMATION: primer

<400> SEQUENCE: 42
ttagagtgca gcagggacac                                                      20

<210> SEQ ID NO 43
<211> LENGTH: 21
<212> TYPE: DNA
<213> ORGANISM: Artificial Sequence
<220> FEATURE:
<223> OTHER INFORMATION: primer

<400> SEQUENCE: 43
cattcgacgt tagagggact g                                                    21

<210> SEQ ID NO 44
<211> LENGTH: 40

```
<212> TYPE: DNA
<213> ORGANISM: Artificial Sequence
<220> FEATURE:
<223> OTHER INFORMATION: primer

<400> SEQUENCE: 44
aaaaaaaaaa aaaaaatagt ccccgaaaat gcccgttgat                              40

<210> SEQ ID NO 45
<211> LENGTH: 24
<212> TYPE: DNA
<213> ORGANISM: Artificial Sequence
<220> FEATURE:
<223> OTHER INFORMATION: primer

<400> SEQUENCE: 45
aatttcgagt gtgatcagaa acct                                              24

<210> SEQ ID NO 46
<211> LENGTH: 21
<212> TYPE: DNA
<213> ORGANISM: Artificial Sequence
<220> FEATURE:
<223> OTHER INFORMATION: primer

<400> SEQUENCE: 46
cgaaaacctt ctgttctgtg g                                                 21

<210> SEQ ID NO 47
<211> LENGTH: 20
<212> TYPE: DNA
<213> ORGANISM: Artificial Sequence
<220> FEATURE:
<223> OTHER INFORMATION: primer

<400> SEQUENCE: 47
cggagcgtaa ccactttctt                                                   20

<210> SEQ ID NO 48
<211> LENGTH: 21
<212> TYPE: DNA
<213> ORGANISM: Artificial Sequence
<220> FEATURE:
<223> OTHER INFORMATION: primer

<400> SEQUENCE: 48
ttcgttcgtt cacttcgttc t                                                 21

<210> SEQ ID NO 49
<211> LENGTH: 40
<212> TYPE: DNA
<213> ORGANISM: Artificial Sequence
<220> FEATURE:
<223> OTHER INFORMATION: primer

<400> SEQUENCE: 49
aggcagtgga ttgtgaatcc accatgcgcg ggttcaagtc                             40

<210> SEQ ID NO 50
<211> LENGTH: 21
<212> TYPE: DNA
<213> ORGANISM: Artificial Sequence
<220> FEATURE:
<223> OTHER INFORMATION: primer

<400> SEQUENCE: 50
```
aggcctttcc ttaagcttcc t                                              21

<210> SEQ ID NO 51
<211> LENGTH: 40
<212> TYPE: DNA
<213> ORGANISM: Artificial Sequence
<220> FEATURE:
<223> OTHER INFORMATION: primer

<400> SEQUENCE: 51
ccagctggaa ctattgactt tacaccctct accgcaggtt                          40

<210> SEQ ID NO 52
<211> LENGTH: 22
<212> TYPE: DNA
<213> ORGANISM: Artificial Sequence
<220> FEATURE:
<223> OTHER INFORMATION: primer

<400> SEQUENCE: 52
gataactcca gtgggcaaga ac                                             22

<210> SEQ ID NO 53
<211> LENGTH: 21
<212> TYPE: DNA
<213> ORGANISM: Artificial Sequence
<220> FEATURE:
<223> OTHER INFORMATION: primer

<400> SEQUENCE: 53
agtggacttc cttcctttcc a                                              21

<210> SEQ ID NO 54
<211> LENGTH: 40
<212> TYPE: DNA
<213> ORGANISM: Artificial Sequence
<220> FEATURE:
<223> OTHER INFORMATION: primer

<400> SEQUENCE: 54
tttttttttt ttttgggaac tttgtaatta agccgaaaga                          40

<210> SEQ ID NO 55
<211> LENGTH: 20
<212> TYPE: DNA
<213> ORGANISM: Artificial Sequence
<220> FEATURE:
<223> OTHER INFORMATION: primer

<400> SEQUENCE: 55
attccccacc caaccaatac                                                20

<210> SEQ ID NO 56
<211> LENGTH: 21
<212> TYPE: DNA
<213> ORGANISM: Artificial Sequence
<220> FEATURE:
<223> OTHER INFORMATION: primer

<400> SEQUENCE: 56
aagagcagct ttctccgttc t                                              21

<210> SEQ ID NO 57
<211> LENGTH: 20
<212> TYPE: DNA
<213> ORGANISM: Artificial Sequence

```
<220> FEATURE:
<223> OTHER INFORMATION: primer

<400> SEQUENCE: 57
gggctcgaca aaacagaaag                                                 20

<210> SEQ ID NO 58
<211> LENGTH: 20
<212> TYPE: DNA
<213> ORGANISM: Artificial Sequence
<220> FEATURE:
<223> OTHER INFORMATION: primer

<400> SEQUENCE: 58
gcccacttct tcacatccac                                                 20

<210> SEQ ID NO 59
<211> LENGTH: 40
<212> TYPE: DNA
<213> ORGANISM: Artificial Sequence
<220> FEATURE:
<223> OTHER INFORMATION: primer

<400> SEQUENCE: 59
ttcagtgtct caaaagagaa ttgcttctat caagataggc                           40

<210> SEQ ID NO 60
<211> LENGTH: 21
<212> TYPE: DNA
<213> ORGANISM: Artificial Sequence
<220> FEATURE:
<223> OTHER INFORMATION: primer

<400> SEQUENCE: 60
agaaggagaa ggctgagaac g                                               21

<210> SEQ ID NO 61
<211> LENGTH: 19
<212> TYPE: DNA
<213> ORGANISM: Artificial Sequence
<220> FEATURE:
<223> OTHER INFORMATION: primer

<400> SEQUENCE: 61
cggttctttc gggtttgat                                                  19

<210> SEQ ID NO 62
<211> LENGTH: 20
<212> TYPE: DNA
<213> ORGANISM: Artificial Sequence
<220> FEATURE:
<223> OTHER INFORMATION: primer

<400> SEQUENCE: 62
ccagggatgg acgtaaactc                                                 20

<210> SEQ ID NO 63
<211> LENGTH: 20
<212> TYPE: DNA
<213> ORGANISM: Artificial Sequence
<220> FEATURE:
<223> OTHER INFORMATION: primer

<400> SEQUENCE: 63
actgacccgt ctcgtatcgt                                                 20
```

<210> SEQ ID NO 64
<211> LENGTH: 20
<212> TYPE: DNA
<213> ORGANISM: Artificial Sequence
<220> FEATURE:
<223> OTHER INFORMATION: primer

<400> SEQUENCE: 64
gacgagtgga atgagggaga                                                    20

<210> SEQ ID NO 65
<211> LENGTH: 20
<212> TYPE: DNA
<213> ORGANISM: Artificial Sequence
<220> FEATURE:
<223> OTHER INFORMATION: primer

<400> SEQUENCE: 65
ttcgttagtt ccgcagctct                                                    20

<210> SEQ ID NO 66
<211> LENGTH: 40
<212> TYPE: DNA
<213> ORGANISM: Artificial Sequence
<220> FEATURE:
<223> OTHER INFORMATION: primer

<400> SEQUENCE: 66
aaaaaaaaaa aaaagcaggt agcttgaccg ccttacgagt                              40

<210> SEQ ID NO 67
<211> LENGTH: 21
<212> TYPE: DNA
<213> ORGANISM: Artificial Sequence
<220> FEATURE:
<223> OTHER INFORMATION: primer

<400> SEQUENCE: 67
aagccgacgt taatagcagg t                                                  21

<210> SEQ ID NO 68
<211> LENGTH: 25
<212> TYPE: DNA
<213> ORGANISM: Artificial Sequence
<220> FEATURE:
<223> OTHER INFORMATION: primer

<400> SEQUENCE: 68
gtggaattcc tactctcatc tcttt                                              25

<210> SEQ ID NO 69
<211> LENGTH: 40
<212> TYPE: DNA
<213> ORGANISM: Artificial Sequence
<220> FEATURE:
<223> OTHER INFORMATION: primer

<400> SEQUENCE: 69
atgagttctc accttctctc atggagtagg tagatgagtc                              40

<210> SEQ ID NO 70
<211> LENGTH: 40
<212> TYPE: DNA
<213> ORGANISM: Artificial Sequence
<220> FEATURE:
<223> OTHER INFORMATION: primer

<400> SEQUENCE: 70
tttttttttt tttttttaca cgggaatgag aacaaaagga        40

<210> SEQ ID NO 71
<211> LENGTH: 40
<212> TYPE: DNA
<213> ORGANISM: Artificial Sequence
<220> FEATURE:
<223> OTHER INFORMATION: primer

<400> SEQUENCE: 71
atgagttctc accttctctc atggagtagg tagatgagac        40

<210> SEQ ID NO 72
<211> LENGTH: 20
<212> TYPE: DNA
<213> ORGANISM: Artificial Sequence
<220> FEATURE:
<223> OTHER INFORMATION: primer

<400> SEQUENCE: 72
tgagcctgat gagttgacca        20

<210> SEQ ID NO 73
<211> LENGTH: 21
<212> TYPE: DNA
<213> ORGANISM: Artificial Sequence
<220> FEATURE:
<223> OTHER INFORMATION: primer

<400> SEQUENCE: 73
gctcgcttcg aaagaaagaa c        21

<210> SEQ ID NO 74
<211> LENGTH: 21
<212> TYPE: DNA
<213> ORGANISM: Artificial Sequence
<220> FEATURE:
<223> OTHER INFORMATION: primer

<400> SEQUENCE: 74
ggaaggatcg aaccatagga a        21

<210> SEQ ID NO 75
<211> LENGTH: 22
<212> TYPE: DNA
<213> ORGANISM: Artificial Sequence
<220> FEATURE:
<223> OTHER INFORMATION: primer

<400> SEQUENCE: 75
ttgatgagcc tttacgagtt ga        22

<210> SEQ ID NO 76
<211> LENGTH: 20
<212> TYPE: DNA
<213> ORGANISM: Artificial Sequence
<220> FEATURE:
<223> OTHER INFORMATION: primer

<400> SEQUENCE: 76
acttggccgg aaagtgttct        20

<210> SEQ ID NO 77

```
<211> LENGTH: 40
<212> TYPE: DNA
<213> ORGANISM: Artificial Sequence
<220> FEATURE:
<223> OTHER INFORMATION: primer

<400> SEQUENCE: 77
tttttttttt ttttggcatt ttcggggact agcccggtac                              40

<210> SEQ ID NO 78
<211> LENGTH: 21
<212> TYPE: DNA
<213> ORGANISM: Artificial Sequence
<220> FEATURE:
<223> OTHER INFORMATION: primer

<400> SEQUENCE: 78
tagaaaggga ggacaggttg g                                                  21

<210> SEQ ID NO 79
<211> LENGTH: 40
<212> TYPE: DNA
<213> ORGANISM: Artificial Sequence
<220> FEATURE:
<223> OTHER INFORMATION: primer

<400> SEQUENCE: 79
aaaaaaaagg aaagaacaat gtacatggac caggtgacta                              40

<210> SEQ ID NO 80
<211> LENGTH: 40
<212> TYPE: DNA
<213> ORGANISM: Artificial Sequence
<220> FEATURE:
<223> OTHER INFORMATION: primer

<400> SEQUENCE: 80
gtactgacca caccgagggg caggccctga agcgaacgac                              40

<210> SEQ ID NO 81
<211> LENGTH: 22
<212> TYPE: DNA
<213> ORGANISM: Artificial Sequence
<220> FEATURE:
<223> OTHER INFORMATION: primer

<400> SEQUENCE: 81
gcagggatac atgcataaac ag                                                 22

<210> SEQ ID NO 82
<211> LENGTH: 21
<212> TYPE: DNA
<213> ORGANISM: Artificial Sequence
<220> FEATURE:
<223> OTHER INFORMATION: primer

<400> SEQUENCE: 82
gttcgattca tgatcgcatc t                                                  21

<210> SEQ ID NO 83
<211> LENGTH: 21
<212> TYPE: DNA
<213> ORGANISM: Artificial Sequence
<220> FEATURE:
<223> OTHER INFORMATION: primer

<400> SEQUENCE: 83
```

-continued

```
tttcaggcag tggccgttta g                                             21

<210> SEQ ID NO 84
<211> LENGTH: 20
<212> TYPE: DNA
<213> ORGANISM: Artificial Sequence
<220> FEATURE:
<223> OTHER INFORMATION: primer

<400> SEQUENCE: 84
ttgctgtatc ggaaagtcca                                               20

<210> SEQ ID NO 85
<211> LENGTH: 20
<212> TYPE: DNA
<213> ORGANISM: Artificial Sequence
<220> FEATURE:
<223> OTHER INFORMATION: primer

<400> SEQUENCE: 85
gcatgtcgta agcgagtcaa                                               20

<210> SEQ ID NO 86
<211> LENGTH: 21
<212> TYPE: DNA
<213> ORGANISM: Artificial Sequence
<220> FEATURE:
<223> OTHER INFORMATION: primer

<400> SEQUENCE: 86
taggcccatc cacctcacta t                                             21

<210> SEQ ID NO 87
<211> LENGTH: 40
<212> TYPE: DNA
<213> ORGANISM: Artificial Sequence
<220> FEATURE:
<223> OTHER INFORMATION: primer

<400> SEQUENCE: 87
tttttttttt cccatgttaa caatctcaat gttgctaaag                         40

<210> SEQ ID NO 88
<211> LENGTH: 40
<212> TYPE: DNA
<213> ORGANISM: Artificial Sequence
<220> FEATURE:
<223> OTHER INFORMATION: primer

<400> SEQUENCE: 88
gggtttccta cgacattcca cttgcggaat ggaataaaag                         40

<210> SEQ ID NO 89
<211> LENGTH: 20
<212> TYPE: DNA
<213> ORGANISM: Artificial Sequence
<220> FEATURE:
<223> OTHER INFORMATION: primer

<400> SEQUENCE: 89
gcaaagcggg aaatccttac                                               20

<210> SEQ ID NO 90
<211> LENGTH: 40
<212> TYPE: DNA
```

```
<213> ORGANISM: Artificial Sequence
<220> FEATURE:
<223> OTHER INFORMATION: primer

<400> SEQUENCE: 90
aaaaaaaaaa aaaaacgaga gactggcgtt ccacgaggac          40

<210> SEQ ID NO 91
<211> LENGTH: 20
<212> TYPE: DNA
<213> ORGANISM: Artificial Sequence
<220> FEATURE:
<223> OTHER INFORMATION: primer

<400> SEQUENCE: 91
ggcagtcaga ccaactctca                                20

<210> SEQ ID NO 92
<211> LENGTH: 20
<212> TYPE: DNA
<213> ORGANISM: Artificial Sequence
<220> FEATURE:
<223> OTHER INFORMATION: primer

<400> SEQUENCE: 92
atcggtccac acagttgtcc                                20
```